US010952940B2

(12) United States Patent
Sarikaya et al.

(10) Patent No.: US 10,952,940 B2
(45) Date of Patent: Mar. 23, 2021

(54) REAGENTS AND METHODS FOR MINERALIZATION OF TOOTH ENAMEL

(71) Applicant: UNIVERSITY OF WASHINGTON, Seattle, WA (US)

(72) Inventors: Mehmet Sarikaya, Seattle, WA (US); Sami Dogan, Seattle, WA (US); Hanson Fong, Seattle, WA (US); Deniz Yucesoy, Seattle, WA (US)

(73) Assignee: University of Washington, Seattle, WA (US)

( * ) Notice: Subject to any disclaimer, the term of this patent is extended or adjusted under 35 U.S.C. 154(b) by 135 days.

(21) Appl. No.: 16/070,129

(22) PCT Filed: Jan. 13, 2017

(86) PCT No.: PCT/US2017/013492
§ 371 (c)(1),
(2) Date: Jul. 13, 2018

(87) PCT Pub. No.: WO2017/123986
PCT Pub. Date: Jul. 20, 2017

(65) Prior Publication Data
US 2019/0380929 A1    Dec. 19, 2019

Related U.S. Application Data

(60) Provisional application No. 62/279,418, filed on Jan. 15, 2016.

(51) Int. Cl.
*A61K 8/24* (2006.01)
*A61K 8/64* (2006.01)
*A61K 8/21* (2006.01)
*A61Q 11/00* (2006.01)

(52) U.S. Cl.
CPC ............ *A61K 8/24* (2013.01); *A61K 8/21* (2013.01); *A61K 8/64* (2013.01); *A61K 2800/86* (2013.01); *A61Q 11/00* (2013.01)

(58) Field of Classification Search
CPC ........ A61K 2800/86; A61K 8/19; A61K 8/21; A61K 8/24; A61K 8/64; A61Q 11/00
See application file for complete search history.

(56) References Cited

U.S. PATENT DOCUMENTS

| 7,078,021 B2 | 7/2006 | Yoneda et al. |
| 7,294,352 B2 | 11/2007 | Gestrelius et al. |
| 2014/0186273 A1* | 7/2014 | Moradian-Oldak ... A61K 8/736 424/50 |

FOREIGN PATENT DOCUMENTS

| EP | 2853256 A1 | 4/2015 |
| WO | 2012/166626 A1 | 12/2012 |
| WO | 2016/115283 A2 | 7/2016 |

OTHER PUBLICATIONS

Amelogenin, UniProtKB—Q62557, Uniprot Protein Database, accessed on Apr. 8, 2020.*
WIPO Translation, WO2012166626_Description, accessed on Apr. 8, 2020.*
WIPO Translation, WO2012166626_Claims, accessed on Apr. 8, 2020.*
Ammari, et al., "Systematic review of studies comparing the anti-caries efficacy of children's toothpaste containing 600 ppm of fluoride or less with high fluoride toothpastes of 1,000 ppm or above," Caries Res, vol. 37, No. 2, pp. 85-92, 2003.
Aponte-Merced, "Uptake of 45Ca from a topically-applied monofluorophosphate sodium fluoride calcium hydroxide dentifrice by rat enamel," Archs Oral Biol, vol. 32, No. 1, pp. 17-20, 1987.
Borges, et al. "Influence of remineralizing gels on bleached enamel microhardness in different time intervals," Operative Dentistry, vol. 35, No. 2, pp. 180-186, 2010.
Brunton, et al., "Treatment of early caries lesions using biomimetic self-assembling peptides—a clinical safety trial," British Dental Journal, vol. 215, No. 4, 6 pages, 2013.
Chen, F., et al., "Novel Technologies for the Prevention and Treatment of Dental Caries: A Patent Survey," Expert Opinion on Therapeutic Patents, vol. 20, No. 5, pp. 681-694, 2018.
Fan, et al, "Controlled Remineralization of Enamel in the Presence of Amelogenin and Fluoride," Biomaterials, vol. 30, Issue 4, pp. 478-483, 2019.
Fan, et al., "Amelogenin-Assisted Ex Vivo Remineralization of Human Enamel: Effects of Supersaturation Degree and Fluoride Concentration," Acta Biomaterialia, vol. 7, Issue 5, pp. 2293-2302, 2011.
Featherstone, et al., "The science and practice of caries prevention," J Am Dent Assoc, vol. 131, No. 7, pp. 887-899, 2000.
Gaffar, et al., "In vivo studies with a dicalcium phosphate dihydrate/ MFP system for caries prevention," International Dental Journal, vol. 43, 1 Suppl 1, pp. 81-88, 1993.
Gungormus, et al. "Cementomimetics—constructing a cementum-like biomineralized microlayer via amelogenin-derived peptides," International Journal of Oral Science, vol. 4, No. 2, pp. 69-77, 2012.
Huang, et al., "Combined effects of nano-hydroxyapatite and Galla chinensis on remineralization of initial enamel lesion in vitro," Journal of Dentistry, vol. 38, No. 10, pp. 811-819, 2010.
Huang, et al., "Effect of nano-hydroxyapatite concentration on remineralization of initial enamel lesion in vitro," Biomedical Materials, vol. 4, No. 3, 6 pages, 2009.
Huang, et al., "Remineralization potential of nano-hydroxyapatite on initial enamel lesions: an in vitro study," Caries Research, vol. 45, No. 5, pp. 460-468, 2011.
Ieong, et al., "Possibilities and Potential Roles of the Functional Peptides Based on Enamel Matrix Proteins in Promoting the Remineralization of Initial Enamel Caries," Medical Hypotheses, vol. 76, Issue 3, pp. 391-394, 2011.
Iijima, et al., "Acid resistance of enamel subsurface lesions remineralized by a sugar-free chewing gum containing casein phosphopeptide-amorphous calcium phosphate," Caries Res, vol. 38, No. 6, pp. 551-556, 2004.

(Continued)

*Primary Examiner* — James H Alstrum-Acevedo
*Assistant Examiner* — Erinne R Dabkowski
(74) *Attorney, Agent, or Firm* — McDonnell Boehnen Hulbert and Berghoff LLP

(57) ABSTRACT

Reagents and methods for whitening and remineralizing teeth using biomineralizing peptides are described.

19 Claims, 13 Drawing Sheets
Specification includes a Sequence Listing.

(56) References Cited

OTHER PUBLICATIONS

Iijima, et al., "In vitro remineralization of in vivo and in vitro formed enamel lesions," Caries Res, vol. 33, No. 3, pp. 206-213, 1999.
Ingram, et al., "A chemical and histological study of artificial caries in human dental enamel in vitro," Caries Res, vol. 15, No. 5, pp. 393-398, 1981.
Koulourides, et al., "Rehardening of softened enamel surfaces of human teeth by solutions of calcium phosphates," Nature, vol. 189, pp. 226-227, 1961.
Liang, et al., "Regeneration of Biomimetic Hydroxyapatite on Etched Human Enamel by Anionic PAMAM Template in vitro," Archives of Oral Biology, vol. 58, Issue 8, pp. 975-980, 2013.
Lin, et al., "Evaluation of the effect of laser tooth whitening" International Journal of Prosthodontics, vol. 21, No. 5, pp. 415-418, 2008.
Nakashima, et al., "Effect of a test dentifrice containing nano-sized calcium carbonate on remineralization of enamel lesions in vitro," Journal of Oral Science, vol. 51, 1, pp. 69-77, 2009.
Oren, et al., "A novel knowledge-based approach to design inorganic-binding peptides," Bioinformatics, vol. 23, No. 21, pp. 2816-2822, 2007.
Paine, et al "Regulated gene expression dictates enamel structure and tooth function," Matrix Biology, vol. 20, No. 5-6, pp. 273-292, 2001.
Patel, et al., "An in vitro comparison of tooth whitening techniques on natural tooth colour," British Dental Journal 204, No. 9, 2008.
PCT/US2016/013301—International Search Report & Written Opinion, 2016.
Petersson, et al., "Professional fluoride varnish treatment for caries control: a systematic review of clinical trials," Acta Odontol Scand, vol. 62, No. 3, pp. 170-176, 2004.
Reynolds, et al., "Fluoride and casein phosphopeptide-amorphous calcium phosphate," J Dent Res, vol. 87, No. 4, pp. 344-348, 2008.
Roberts, "Role of models in assessing new agents for caries prevention—non-fluoride systems," Adv Dent Res, vol. 9, No. 3, pp. 304-311, discussion 312-4, 1995.
Selwitz, et al., "Dental caries," The Lancet, vol. Jan 6; vol. 369, No. 9555, pp. 51-59, 2007.
Shen, et al., "Remineralization of enamel subsurface lesions by sugar-free chewing gum containing casein phosphopeptide-amorphous calcium phosphate," J Dent Res, vol. 80, No. 12, pp. 2066-2070, 2001.
Silverstone, et al., "Remineralization of natural and artificial lesions in human dental enamel in vitro. Effect of calcium concentration of the calcifying fluid," Caries Res, vol. 15, No. 2, pp. 138-157, 1981.
St John, "Biocompatibility of dental materials," Dental Clinics of North America, vol. 51, No. 3, pp. 747-760, 2007.
Steiner, et al., "Fluoride as an essential element in the prevention of disease," Med Hypotheses, vol. 62, No. 5, pp. 710-717, 2004.
Sulieman, et al., "Development and evaluation of a method in vitro to study the effectiveness of tooth bleaching," Journal of Dentistry, vol. 31, No. 6, pp. 415-422, 2003.
Sullivan, et al., "Development of an enhanced anticaries efficacy dual component dentifrice containing sodium fluoride and dicalcium phosphate dehydrate," American Journal of Dentistry, vol. 14, Spec No. 3A-11A, 2001.
Ten Cate, et al., "Mechanistic Aspects of the Interactions Between Fluoride and Dental Enamel", Critical Reviews in Oral Biology and Medicine, vol. 2, No. 2, pp. 283-296, 1991.
Ten Cate, et al., "Remineralization of artificial enamel lesions in vitro.II. Determination of activation energy and reaction order," Caries Res, vol. 12, No. 4, pp. 213-222, 1978.
Ten Cate, et al., "Remineralization of artificial enamel lesions in vitro: III. A study of the deposition mechanism," Caries Res. vol. 14, No. 6, pp. 351-358, 1980.
Ten Cate, et al., "Remineralization of artificial enamel lesions in vitro. IV. Influence of fluorides and diphosphonates on short- and long-term remineralization," Caries Res, vol. 15, No. 1, pp. 60-69, 1981.
Twetman, et al., "Caries-preventive effect of fluoride toothpaste: a systematic review," Acta Odontologica Scandinavica, vol. 61, No. 6, pp. 347-355, 2003.
Watts, et al. "Tooth discolouration and staining: a review of the literature," British Dental Journal, vol. 190, No. 6, pp. 309-316, 2001.
Wefel, et al., "Development of an intra-oral single-section remineralization model," J Dent Res, vol. 66, No. 9, pp. 1485-1489, 1987.
Wefel, et al., "The use of saturated DCPD in remineralization of artificial caries lesions in vitro," J Dent Res, vol. 66, No. 11, pp. 1640-1643, 1987.
Yamagishi, et al., "A synthetic enamel for rapid tooth repair," Nature, vol. 433, No. 7028, p. 819, 2005.
The International Search Report (ISR) with Written Opinion for PCT/US2017/013492 dated Jun. 8, 2017, pp. 1-24.
Gungormus, Mustafa et al. "Cementomimetics—constructing a cementum-like biomineralized microlayer via amelogenin-derived peptides" International Journal of Oral Science (2012) vol. 4, pp. 69-77.

* cited by examiner

SEQUENCE LISTING

```
<160> NUMBER OF SEQ ID NOS: 24

<210> SEQ ID NO 1
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: X is L or I

<400> SEQUENCE: 1

His Thr Leu Gln Pro His His His Xaa Pro Val Val
1               5                   10

<210> SEQ ID NO 2
<211> LENGTH: 12
<212> TYPE: PRT
<213> ORGANISM: Artificial Sequence
```

```
<220> FEATURE:
<223> OTHER INFORMATION: Synthetic

<400> SEQUENCE: 2

His Thr Leu Gln Pro His His His Leu Pro Val Val
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

His Thr Leu Gln Pro His His His Ile Pro Val Val
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is H or Q
<220> FEATURE:
<221> NAME/KEY: MISC_FEATURE
<222> LOCATION: (10)..(10)
<223> OTHER INFORMATION: X is T or I

<400> SEQUENCE: 4

Val Pro Gly Xaa His Ser Met Thr Pro Xaa Gln His
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Val Pro Gly His His Ser Met Thr Pro Thr Gln His
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Val Pro Gly Gln His Ser Met Thr Pro Ile Gln His
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or S
```

```
<400> SEQUENCE: 7

Trp Pro Xaa Thr Asp Lys Thr Lys Arg Glu Glu Val Asp
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8

Trp Pro Ala Thr Asp Lys Thr Lys Arg Glu Glu Val Asp
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic

<400> SEQUENCE: 9

Trp Pro Ser Thr Asp Lys Thr Lys Arg Glu Glu Val Asp
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is S or T
<220> FEATURE:
<221> NAME/KEY: MISC_FEATURE
<222> LOCATION: (13)..(13)
<223> OTHER INFORMATION: X is L or I

<400> SEQUENCE: 10

His Pro Pro Xaa His Thr Leu Gln Pro His His His Xaa Pro Val Val
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic

<400> SEQUENCE: 11

His Pro Pro Ser His Thr Leu Gln Pro His His His Leu Pro Val Val
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic

<400> SEQUENCE: 12

His Pro Pro Thr His Thr Leu Gln Pro His His His Ile Pro Val Val
1               5                   10                  15
```

```
<210> SEQ ID NO 13
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is L or F
<220> FEATURE:
<221> NAME/KEY: MISC_FEATURE
<222> LOCATION: (10)..(10)
<223> OTHER INFORMATION: X is K or N
<220> FEATURE:
<221> NAME/KEY: MISC_FEATURE
<222> LOCATION: (18)..(18)
<223> OTHER INFORMATION: X is T or V

<400> SEQUENCE: 13

Pro Gly Tyr Ile Asn Xaa Ser Tyr Glu Xaa Ser His Ser Gln Ala Ile
1               5                   10                  15

Asn Xaa Asp Arg Thr Ala
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic

<400> SEQUENCE: 14

Pro Gly Tyr Ile Asn Leu Ser Tyr Glu Lys Ser His Ser Gln Ala Ile
1               5                   10                  15

Asn Thr Asp Arg Thr Ala
            20

<210> SEQ ID NO 15
<211> LENGTH: 22
<212> TYPE: PRT
<213> ORGANISM: Artificial Sequence
<220> FEATURE:
<223> OTHER INFORMATION: Synthetic

<400> SEQUENCE: 15

Pro Gly Tyr Ile Asn Phe Ser Tyr Glu Asn Ser His Ser Gln Ala Ile
1               5                   10                  15

Asn Val Asp Arg Thr Ala
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Ser Tyr Glu Asn Ser His Ser Gln Ala Ile Asn Val Asp Arg Thr
1               5                   10                  15

<210> SEQ ID NO 17
<211> LENGTH: 24
<212> TYPE: PRT
<213> ORGANISM: Artificial Sequence
<220> FEATURE:
```

<223> OTHER INFORMATION: Synthetic

<400> SEQUENCE: 17

Leu Pro Pro Leu Phe Ser Met Pro Leu Ser Pro Ile Leu Pro Glu Leu
1               5                   10                  15

Pro Leu Glu Ala Trp Pro Ala Thr
            20

<210> SEQ ID NO 18
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is S or T
<220> FEATURE:
<221> NAME/KEY: MISC_FEATURE
<222> LOCATION: (13)..(13)
<223> OTHER INFORMATION: X is L or I
<220> FEATURE:
<221> NAME/KEY: MISC_FEATURE
<222> LOCATION: (23)..(23)
<223> OTHER INFORMATION: X is A or I
<220> FEATURE:
<221> NAME/KEY: MISC_FEATURE
<222> LOCATION: (34)..(34)
<223> OTHER INFORMATION: X is H or Q
<220> FEATURE:
<221> NAME/KEY: MISC_FEATURE
<222> LOCATION: (40)..(40)
<223> OTHER INFORMATION: X is T or I

<400> SEQUENCE: 18

His Pro Pro Xaa His Thr Leu Gln Pro His His His Xaa Pro Val Val
1               5                   10                  15

Pro Ala Gln Gln Pro Val Xaa Pro Gln Gln Pro Met Met Pro Val Pro
            20                  25                  30

Gly Xaa His Ser Met Thr Pro Xaa Gln His
        35                  40

<210> SEQ ID NO 19
<211> LENGTH: 42
<212> TYPE: PRT
<213> ORGANISM: Artificial Sequence
<220> FEATURE:
<223> OTHER INFORMATION: Synthetic

<400> SEQUENCE: 19

His Pro Pro Ser His Thr Leu Gln Pro His His His Leu Pro Val Val
1               5                   10                  15

Pro Ala Gln Gln Pro Val Ala Pro Gln Gln Pro Met Met Pro Val Pro
            20                  25                  30

Gly His His Ser Met Thr Pro Thr Gln His
        35                  40

<210> SEQ ID NO 20
<211> LENGTH: 42
<212> TYPE: PRT
<213> ORGANISM: Artificial Sequence
<220> FEATURE:
<223> OTHER INFORMATION: Synthetic

<400> SEQUENCE: 20

His Pro Pro Thr His Thr Leu Gln Pro His His His Ile Pro Val Val

```
                1               5                   10                  15
Pro Ala Gln Gln Pro Val Ile Pro Gln Gln Pro Met Met Pro Val Pro
                        20                  25                  30

Gly Gln His Ser Met Thr Pro Ile Gln His
            35                  40

<210> SEQ ID NO 21
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: X is A or I

<400> SEQUENCE: 21

Pro Ala Gln Gln Pro Val Xaa Pro Gln Gln Pro Met Met Pro
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic

<400> SEQUENCE: 22

Pro Ala Gln Gln Pro Val Ala Pro Gln Gln Pro Met Met Pro
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic

<400> SEQUENCE: 23

Pro Ala Gln Gln Pro Val Ile Pro Gln Gln Pro Met Met Pro
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Ser Tyr Glu Lys Ser His Ser Gln Ala Ile Asn Thr Asp Arg Thr
1               5                   10                  15
```

REAGENTS AND METHODS FOR MINERALIZATION OF TOOTH ENAMEL

CROSS-REFERENCE TO RELATED APPLICATIONS

This application claims priority from U.S. Provisional Patent Application Ser. No. 62/279,418 filed Jan. 15, 2016 and PCT application PCT/US2016/013301 filed Jan. 13, 2016, the contents of which are incorporated herein by reference.

BACKGROUND

Accumulation of various chromogens/discolorants, for example, food and tobacco that come into contact daily onto tooth surfaces and their subsequent penetration into deeper regions (dentin), cause tooth discoloration. Furthermore, the process of aging, disease, trauma, certain medications, certain congenital conditions, and environmental effects can also cause teeth to become discolored. Although discolored teeth do not cause health problems, since bright white teeth are usually considered to be cosmetically desirable, there is a great deal of interest in developing compositions and methods for whitening teeth.

There are several techniques for whitening or bleaching of teeth. Professional whitening methods, also known as "in-clinic" whitening strategies, are considered presently as the most effective methods. These in-clinic whitening strategies typically involve the application of high-concentration peroxide products (up to 35%) and other abrasive chemicals to the discolored area. These peroxide species penetrate the stained area (up to underlying dentin layer) and dissolve the accumulated discoloring agents through an oxidation process. To achieve desired effects more quickly, such oxidation reactions on teeth are often assisted with external laser light application, which heats up the reaction site and thereby increases the rate oxidation reaction. Furthermore, utilization of titanium dioxide up to 10% is often preferred to facilitate these photo-catalytic reactions. Other in-clinic whitening techniques involve superficially removing the enamel layer with abrasive instruments or pumice followed by treatment with additional caustic agents.

There are several drawbacks of these in-clinic techniques. First of all, the abrasive chemicals and peroxide agents causes enamel demineralization and results with teeth sensitivity. In most cases sore/injured gums as well as bad taste of the product itself cause much discomfort to the patients. Further, patients are required to make a clinic appointment to get this medical service.

Other existing products for at-home use contain considerably lower concentrations of active oxidizing agents and, thus, are generally less effective than in-clinic whitening strategies and products. Therefore, dramatic whitening effect can only be achieved by the repeated applications of these reagents for several weeks. These treatments often assisted with bleaching trays (night-guard) in order to better localize bleaching products and, thereby, maximize the whitening effect. However, even though these at home products contain active whitening agents in lower concentrations, similar side effects as those associated with professional treatments are very common. In addition, there are paint-on, at-home whitening products, also known as "tooth varnishes", as well as whitening strips intended to eliminate the need for dental trays. However, these products require more frequent applications, usually 3-times in a day, to complete whitening procedure. Finally, among the variety of at-home use products, whitening toothpastes and gels are the least effective form of whitening products due to their short contact time with the tooth surfaces. Although bleaching agent additives augment the effectiveness, the whitening effect is primarily as a result of removal of surface stains via mechanical action of brushing and other polishing ingredients (for example, silica particles).

Dental caries is one of the major public health problems and it is a highly prevalent disease among the global population. Incipient caries and white spot lesions (WSL) as well as hypersensitivity, are the earliest clinical evidence of enamel demineralization and dental caries. Dental caries occurs when tooth enamel is exposed to acid produced by cariogenic bacteria. As a result, acid diffuses into surface enamel and dissolves hydroxyapatite (HAp) mineral. Due to its non-regenerative nature, enamel is unable to heal and repair itself post-demineralization. Traditionally, fluoride (F) has been used as the key agent in prevention of caries. Fluoride functions primarily via topical mechanisms. It is believed that fluoride forms a thin layer of new but harder mineral, namely fluorapatite (FAp) which is incorporated into the existing HAp mineral on the tooth surface. There is a trend of enhancing the remineralization effect of fluoride with calcium and phosphate supplementation in high risk individuals. Although controversial, the use of fluoride products remains the primary treatment modality for caries prevention and remineralization, with major limitations regarding the efficacy of these products for the reversal or prevention of dental caries. Fluoride delivery systems, therefore, are not sufficient to overcome the high caries risk especially in younger and elderly population.

There is presently an unmet need for tooth whitening and mineralization methods and products that reduce or eliminate the need for concentrated, abrasive oxidizing agents and attendant side effects such as demineralization-associated tooth sensitivity and gum line injuries.

SUMMARY OF THE INVENTION

Herein we provide methods and compositions for whitening teeth where the natural color of teeth is restored and improved upon by generating newly formed thin mineral layer on discolored tooth surface using one or more biomineralizing polypeptides. Herein we also provide methods and compositions for mineralizing teeth.

In a first aspect, the present application provides a method for whitening teeth, comprising administering to a subject in need thereof an amount effective to whiten the teeth of a biomineralizing polypeptide. In some embodiments, the method for whitening teeth comprises administering to a subject in need thereof an effective amount of a composition comprising a biomineralizing polypeptide. In some embodiments, the biomineralizing polypeptide comprises an amino acid sequence selected from the group consisting of:

(ADP3; SEQ ID NO: 7)
(WP(A/S)TDKTKREEVD)$_{1-10}$;

(ADP5; SEQ ID NO: 13)
(PGYIN(L/F)SYE(K/N)SHSQAIN(T/V)DRTA)$_{1-10}$;

(ADP6; SEQ ID NO: 17)
(LPPLFSMPLSPILPELPLEAWPAT)$_{1-10}$;

(ADP7; SEQ ID NO: 18)
(HPP(S/T)HTLQPHHH(L/I)PVVPAQQPV(A/I)PQQPMMPVPG(H/Q)HSMTP(T/I)QH)$_{1-10}$;

(SYENSHSQAINVDRT)$_{1-10}$; (shADP5; SEQ ID NO: 16)

(SYEKSHSQAINTDRT)$_{1-10}$ (sADP5; SEQ ID NO: 24)
and 12-42 contiguous amino acids of
(HPP(S/T)HTLQPHHH(L/I)PVVPAQQPV(A/I)PQQPMMPVPG (ADP7; SEQ ID NO: 18)
(H/Q)HSMTP(T/I)QH)$_{1-10}$;

or a functional equivalent thereof, or any combination thereof. In some embodiments, the biomineralizing polypeptide comprises the amino acid sequence (PGYIN(L/F)SYE(K/N) SHSQAIN(T/V)DRTA)$_{1-10}$ (ADP5; SEQ ID NO:13), or a functional equivalent thereof. In some embodiments, the biomineralizing polypeptide comprises the amino acid sequence (PGYINFSYENSHSQAINVDRTA)$_{1-10}$ (ADP5H; SEQ ID NO:15), or a functional equivalent thereof. In some embodiments, the biomineralizing polypeptide comprises the amino acid sequence (SYENSHSQAINVDRT)$_{1-10}$ (shADP5; SEQ ID NO:16), or a functional equivalent thereof. In some embodiments, the biomineralizing polypeptide comprises (HPP(S/T)HTLQPHHH(L/I) PVVPAQQPV(A/I)PQ QPMMPVPG(H/Q)HSMTP(T/I) QH)$_{1-10}$ (ADP7; SEQ ID NO:18), 12-42 contiguous amino acids of (HPP(S/T)HTLQPHHH(L/I) PVVPAQQPV(A/I) PQQPMMPVPG(H/Q)HSMTP(T/I)QH)$_{1-10}$ (ADP7), or a functional equivalent thereof. In some embodiments, the biomineralizing polypeptide comprises an amino acid sequence selected from the group consisting of:

(HTLQPHHH(L/I)PVV)$_{1-10}$; (ADP1; SEQ ID NO: 1)

(VPG(H/Q)HSMTP(T/I)QH)$_{1-10}$ (ADP2; SEQ ID NO: 4)

(HPP(S/T)HTLQPHHH(L/I)PVV)$_{1-10}$; (ADP4; SEQ ID NO: 10)

(PAQQPV(A/I)PQQPMMP)$_{1-10}$; (ADP8; SEQ ID NO: 21)

(HPP(S/T)HTLQPHHH(L/I)PVVPAQQPV(A/I)PQQPMMPVPG (ADP7; SEQ ID NO: 18)
(H/Q)HSMTP(T/I)QH)$_{1-10}$;

HTLQPHHHLPVV)$_{1-10}$ (ADP1M; SEQ ID NO: 2)

(HTLQPHHHIPVV)$_{1-10}$; (ADP1H; SEQ ID NO: 3)

(VPGHHSMTPTQH)$_{1-10}$; (ADP2M; SEQ ID NO: 5)

(VPGQHSMTPIQH)$_{1-10}$; (ADP2H; SEQ ID NO: 6)

(HPPSHTLQPHHHLPVV)$_{1-10}$; (ADP4M; SEQ ID NO: 11)

(HPPTHTLQPHHHIPVV)$_{1-10}$; (ADP4H; SEQ ID NO: 12)

(HPPSHTLQPHHHLPVVPAQQPVAPQQPMMPVPGHHSMTPTQH)$_{1-10}$; (ADP7M; SEQ ID NO: 19)

(HPPTHTLQPHHHIPVVPAQQPVIPQQPMMPVPGQHSMTPIQH)$_{1-10}$; (ADP7H; SEQ ID NO: 20)

(PAQQPVAPQQPMMP)$_{1-10}$; (ADP8M; SEQ ID NO: 22)
and (PAQQPVIPQQPMMP)$_{1-10}$; (ADP8H; SEQ ID NO: 23)

or a functional equivalent thereof, or any combination thereof. In some embodiments, the biomineralizing polypeptide comprises an amino acid sequence selected from the group consisting of:

(WPATDKTKREEVD)$_{1-10}$; (ADP3M; SEQ ID NO: 8)
and (WPSTDKTKREEVD)$_{1-10}$, (ADP3H; SEQ ID NO: 9)

or a functional equivalent thereof, or a combination thereof. In some embodiments, the biomineralizing polypeptide comprises one or more fusion peptides, wherein each of the one or more fusion peptides independently comprises two or more amino acid sequences selected from the group consisting of:

(HTLQPHHH(L/I)PVV)$_{1-10}$; (ADP1; SEQ ID NO: 1)

(VPG(H/Q)HSMTP(T/I)QH)$_{1-10}$ (ADP2; SEQ ID NO: 4)

(WP(A/S)TDKTKREEVD)$_{1-10}$ (ADP3; SEQ ID NO: 7)

(HPP(S/T)HTLQPHHH(L/I)PVV)$_{1-10}$; (ADP4; SEQ ID NO: 10)

(PGYIN(L/F)SYE(K/N)SHSQAIN(T/V)DRTA)$_{1-10}$; (ADP5; SEQ ID NO: 13)

(LPPLFSMPLSPILPELPLEAWPAT)$_{1-10}$; (ADP6; SEQ ID NO: 17)

(PAQQPV(A/I)PQQPMMP)$_{1-10}$; (ADP8; SEQ ID NO: 21)

(HPP(S/T)HTLQPHHH(L/I)PVVPAQQPV(A/I)PQQPMMPVPG (ADP7; SEQ ID NO: 18)
(H/Q)HSMTP(T/I)QH)$_{1-10}$;

(HTLQPHHHLPVV)$_{1-10}$; (ADP1M; SEQ ID NO: 2)

(HTLQPHHHIPVV)$_{1-10}$; (ADP1H; SEQ ID NO: 3)

(VPGHHSMTPTQH)$_{1-10}$; (ADP2M; SEQ ID NO: 5)

(VPGQHSMTPIQH)$_{1-10}$; (ADP2H; SEQ ID NO: 6)

(HPPSHTLQPHHHLPVV)$_{1-10}$; (ADP4M; SEQ ID NO: 11)

(HPPTHTLQPHHHIPVV)$_{1-10}$; (ADP4H; SEQ ID NO: 12)

(HPPSHTLQPHHHLPVVPAQQPVAPQQPMMPVPGHHSMTPTQH)$_{1-10}$; (ADP7M; SEQ ID NO: 19)

(HPPTHTLQPHHHIPVVPAQQPVIPQQPMMPVPGQHSMTPIQH$_{1-10}$; (ADP7H; SEQ ID NO: 20)

(PAQQPVAPQQPMMP)$_{1-10}$; (ADP8M; SEQ ID NO: 22)
and (PAQQPVIPQQPMMP)$_{1-10}$; (ADP8H; SEQ ID NO: 23)

or a functional equivalent thereof. In some embodiments, the biomineralizing polypeptide further comprises a fluorescent agent. In some embodiments, the method further comprises applying light to the teeth of the subject, thereby further whitening the teeth. In some embodiments, the light is selected from one of a diode laser; a PAC light; and a halogen light. In some embodiments, the method further comprises administering at least one cleaning agent to the teeth of the subject. In some embodiments, the method further comprises administering hydrogen peroxide, carbamide peroxide, titanium dioxide, nano-hydroxyapatite particles, zirconia powder, or any combination thereof to the teeth of the subject.

In a second aspect, the present application provides an oral care product, comprising at least one biomineralizing polypeptide, at least one calcium ion source, and at least one phosphate ion source. The oral care product can further comprise at least one cleaning agent. In some embodiments, the at least one cleaning agent is selected from the group consisting of hydrogen peroxide, titanium dioxide, carbamide peroxide, nano-hydroxyapatite particles, zirconia powder, or any combination thereof. The calcium ion source is generally any calcium salt. In some embodiments, the calcium ion source is selected from the group consisting of calcium acetate, calcium carbonate, calcium citrate, calcium chloride, calcium gluconate, calcium glycerophosphate, calcium lactate, and calcium phosphate. The phosphate ion source is generally any phosphate salt. In some embodiments, the phosphate ion source is selected from the group consisting of aluminum phosphates, calcium phosphates, potassium phosphates, and sodium phosphates. In some embodiments, the oral care product is selected from the group consisting of toothpaste, toothpowders, mouthwash, gel, dental floss, liquid dentifrices, dental tablets, topical gels, troches, chewing gums, dental pastes, gingival massage creams, gargle tablets, lozenges, tooth trays, tooth varnishes, and food products. In some embodiments, the biomineralizing polypeptide comprises an amino acid sequence selected from the group consisting of:

(WP(A/S)TDKTKREEVD)$_{1-10}$; (ADP3; SEQ ID NO: 7)

(PGYIN(L/F)SYE(K/N)SHSQAIN(T/V)DRTA)$_{1-10}$; (ADP5; SEQ ID NO: 13)

(LPPLFSMPLSPILPELPLEAWPAT)$_{1-10}$; (ADP6; SEQ ID NO: 17)
and (HPP(S/T)HTLQPHHH(L/I)PVVPAQQPV(A/I)PQQPMMPVPG
(H/Q)HSMTP(T/I)QH)$_{1-10}$; (ADP7; SEQ ID NO: 18)

(SYENSHSQAINVDRT)$_{1-10}$; (shADP5; SEQ ID NO: 16)

(SYEKSHSQAINTDRT)$_{1-10}$; (sADP5; SEQ ID NO: 24)
and 12-42 contiguous amino acids of
(HPP(S/T)HTLQPHHH(L/I)PVVPAQQPV(A/I)
PQQPMMPVPG(H/Q)HSMTP(T/I)QH)$_{1-10}$; (ADP7; SEQ ID NO: 18)

or a functional equivalent thereof, or any combination thereof. In some embodiments, the biomineralizing polypeptide comprises the amino acid sequence (PGYINFSYENSHSQAINVDRTA)$_{1-10}$ (ADP5H; SEQ ID NO:15), or a functional equivalent thereof. In some embodiments, the biomineralizing polypeptide comprises the amino acid sequence (SYENSHSQAINVDRT)$_{1-10}$ (shADP5; SEQ ID NO:16), or a functional equivalent thereof. In some embodiments, the biomineralizing polypeptide comprises (HPP(S/T)HTLQPHHH(L/I)PVVPAQQPV(A/I)PQ QPMMPVPG (H/Q)HSMTP(T/I)QH)$_{1-10}$ (ADP7; SEQ ID NO:18), 12-42 contiguous amino acids of (HPP(S/T)HTLQPHHH(L/I) PVVPAQQPV(A/I) PQQPMMPVPG(H/Q)HSMTP (T/I) QH)$_{1-10}$ (ADP7; SEQ ID NO:18), or a functional equivalent thereof. In some embodiments, the biomineralizing polypeptide comprises an amino acid sequence selected from the group consisting of:

(HTLQPHHH(L/I)PVV)$_{1-10}$; (ADP1; SEQ ID NO: 1)

(VPG(H/Q)HSMTP(T/I)QH)$_{1-10}$; (ADP2; SEQ ID NO: 4)

(HPP(S/T)HTLQPHHH(L/I)PVV)$_{1-10}$; (ADP4; SEQ ID NO: 10)

(PAQQPV(A/I)PQQPMMP)$_{1-10}$; (ADP8; SEQ ID NO: 21)

(HPP(S/T)HTLQPHHH(L/I)PVVPAQQPV(A/I)PQQPMMPVPG
(H/Q)HSMTP(T/I)QH)$_{1-10}$; (ADP7; SEQ ID NO: 18)

(HTLQPHHHLPVV)$_{1-10}$; (ADP1M; SEQ ID NO: 2)

(HTLQPHHHIPVV)$_{1-10}$; (ADP1H; SEQ ID NO: 3)

(VPGHHSMTPTQH)$_{1-10}$; (ADP2M; SEQ ID NO: 5)

(VPGQHSMTPIQH)$_{1-10}$; (ADP2H; SEQ ID NO: 6)

(HPPSHTLQPHHHLPVV)$_{1-10}$; (ADP4M; SEQ ID NO: 11)

(HPPTHTLQPHHHIPVV)$_{1-10}$; (ADP4H; SEQ ID NO: 12)

(HPPSHTLQPHHHLPVVPAQQPVAPQQPMMPVPGHHSMTPTQH)$_{1-10}$; (ADP7M; SEQ ID NO: 19)

(HPPTHTLQPHHHIPVVPAQQPVIPQQPMMPVPGQHSMTPIQH$_{1-10}$; (ADP7H; SEQ ID NO: 20)

(PAQQPVAPQQPMMP)$_{1-10}$; (ADP8M; SEQ ID NO: 22)
and (PAQQPVIPQQPMMP)$_{1-10}$; (ADP8H; SEQ ID NO: 23)

or a functional equivalent thereof, or any combination thereof.

In another aspect, the present application provides methods for mineralizing teeth, comprising administering to one or more teeth of a subject in need thereof an effective amount to mineralize teeth of a polypeptide comprising or consisting of the amino acid sequence selected from the group consisting of:

(SYENSHSQAINVDRT)$_{1-10}$; (shADP5; SEQ ID NO: 16)

(SYEKSHSQAINTDRT)$_{1-10}$; (sADP5; SEQ ID NO: 24)

(WP(A/S)TDKTKREEVD)$_{1-10}$; (ADP3; SEQ ID NO: 7)

(PGYIN(L/F)SYE(K/N)SHSQAIN(T/V)DRTA)$_{1-10}$; (ADP5; SEQ ID NO: 13)

(LPPLFSMPLSPILPELPLEAWPAT)$_{1-10}$; (ADP6; SEQ ID NO: 17)

(HPP(S/T)HTLQPHHH(L/I)PVVPAQ
QPV(A/I)PQQPMMPVPG(H/Q)HSMTP(T/I)QH)$_{1-10}$; (ADP7; SEQ ID NO: 18)
and 12-42 contiguous amino acids of
(HPP(S/T)HTLQPHHH(L/I)PVVPAQQPV(A/I)
PQQPMMPVPG(H/Q)HSMTP(T/I)QH)$_{1-10}$; (ADP7; SEQ ID NO: 18)

or a functional equivalent thereof, or any combination thereof.

In various embodiments, the polypeptide comprises or consists of an amino acid sequence selected from the group consisting of:

(HTLQPHHH(L/I)PVV)$_{1-10}$; (ADP1; SEQ ID NO: 1)

(VPG(H/Q)HSMTP(T/I)QH)$_{1-10}$; (ADP2; SEQ ID NO: 4)

(HPP(S/T)HTLQPHHH(L/I)PVV)$_{1-10}$; (ADP4; SEQ ID NO: 10)

(PAQQPV(A/I)PQQPMMP)$_{1-10}$; (ADP8; SEQ ID NO: 21)

(HPP(S/T)HTLQPHHH(L/I)PVVPAQQPV(A/I)PQQPMMPVPG
(H/Q)HSMTP(T/I)QH)$_{1-10}$; (ADP7; SEQ ID NO: 18)

(HTLQPHHHLPVV)$_{1-10}$; (ADP1M; SEQ ID NO: 2)

(HTLQPHHHIPVV)$_{1-10}$; (ADP1H; SEQ ID NO: 3)

(VPGHHSMTPTQH)$_{1-10}$; (ADP2M; SEQ ID NO: 5)

(VPGQHSMTPIQH)$_{1-10}$; (ADP2H; SEQ ID NO: 6)

(HPPSHTLQPHHHLPVV)$_{1-10}$; (ADP4M; SEQ ID NO: 11)

(HPPTHTLQPHHHIPVV)$_{1-10}$; (ADP4H; SEQ ID NO: 12)

(HPPSHTLQPHHHLPVVPAQQPVAPQQPMMPVPGHHSMTPTQH)$_{1-10}$; (ADP7M; SEQ ID NO: 19)

(HPPTHTLQPHHHIPVVPAQQPVIPQQPMMPVPGQHSMTPIQH$_{1-10}$; (ADP7H; SEQ ID NO: 20)

(PAQQPVAPQQPMMP)$_{1-10}$; (ADP8M; SEQ ID NO: 22)
and (PAQQPVIPQQPMMP)$_{1-10}$; (ADP8H; SEQ ID NO: 23)

(WPATDKTKREEVD)$_{1-10}$; (ADP3M; SEQ ID NO: 8)
and (WPSTDKTKREEVD)$_{1-10}$; (ADP3H; SEQ ID NO: 9)

or a functional equivalent thereof, or a combination thereof.

In various embodiment, the polypeptide comprises a fusion polypeptide comprising two or more of the amino acid sequences selected from the group consisting of:

(SYENSHSQAINVDRT)$_{1-10}$; (shADP5; SEQ ID NO: 16)

(SYEKSHSQAINTDRT)$_{1-10}$ (sADP5; SEQ ID NO: 24)

(HTLQPHHH(L/I)PVV)$_{1-10}$; (ADP1; SEQ ID NO: 1)

(VPG(H/Q)HSMTP(T/I)QH)$_{1-10}$; (ADP2; SEQ ID NO: 4)

(WP(A/S)TDKTKREEVD)$_{1-10}$; (ADP3; SEQ ID NO: 7)

(HPP(S/T)HTLQPHHH(L/I)PVV)$_{1-10}$; (ADP4; SEQ ID NO: 10)

(PGYIN(L/F)SYE(K/N)SHSQAIN(T/V)DRTA)$_{1-10}$; (ADP5; SEQ ID NO: 13)

(LPPLFSMPLSPILPELPLEAWPAT)$_{1-10}$; (ADP6; SEQ ID NO: 17)

(PAQQPV(A/I)PQQPMMP)$_{1-10}$; (ADP8; SEQ ID NO: 21)

(HPP(S/T)HTLQPHHH(L/I)PVVPAQQPV(A/I)PQQPMMPVPG
(H/Q)HSMTP(T/I)QH)$_{1-10}$; (ADP7; SEQ ID NO: 18)

HTLQPHHHLPVV)$_{1-10}$; (ADP1M; SEQ ID NO: 2)

(HTLQPHHHIPVV)$_{1-10}$; (ADP1H; SEQ ID NO: 3)

(VPGHHSMTPTQH)$_{1-10}$; (ADP2M; SEQ ID NO: 5)

(VPGQHSMTPIQH)$_{1-10}$; (ADP2H; SEQ ID NO: 6)

(HPPSHTLQPHHHLPVV)$_{1-10}$; (ADP4M; SEQ ID NO: 11)

(HPPTHTLQPHHHIPVV)$_{1-10}$; (ADP4H; SEQ ID NO: 12)

(HPPSHTLQPHHHLPVVPAQQPVAPQQPMMPVPGHHSMTPTQH)$_{1-10}$; (ADP7M; SEQ ID NO: 19)

(HPPTHTLQPHHHIPVVPAQQPVIPQQPMMPVPGQHSMTPIQH)$_{1-10}$; (ADP7H; SEQ ID NO: 20)

(PAQQPVAPQQPMMP)$_{1-10}$; (ADP8M; SEQ ID NO: 22)
and

-continued (PAQQPVIPQQPMMP)$_{1-10}$; (ADP8H; SEQ ID NO: 23)

or a functional equivalent thereof.

In other embodiments, the polypeptide may be used as a single copy of the polypeptide.

In a further embodiment, the method further comprises administering to the subject at least one calcium ion source and at least one phosphate ion source. In various embodiments, the calcium ion source may be selected from the group consisting of calcium acetate, calcium carbonate, calcium citrate, calcium chloride, calcium gluconate, calcium glycerophosphate, calcium lactate, and calcium phosphate. In various other embodiments, the phosphate ion source may be selected from the group consisting of aluminum phosphates, calcium phosphates, potassium phosphates, and sodium phosphates. In one embodiment, the method comprising administering a formulation of the polypeptide, at least one calcium ion source and at least one phosphate ion source, wherein the formulation has (a) a $Ca^{2+}$ concentration ranging between about 1 mM and about 2 M, or between about 1 mM and about 1M, between about 1 mM and about 0.5M, between about 1 mM and about 100 mM, between about 1 mM and about 50 mM, between about 1 mM and about 10 mM, between about 2 mM and about 8 mM, between about 3 mM and about 7 mM, between about 4 mM and about 6 mM, or between about 4.5 mM and about 5.5 mM; and (b) a $PO_4^{3-}$ concentration ranging between about 0.5 mM and about 2 M, or between about 0.5 mM and about 1M, between about 0.5 mM and about 0.5M, between about 0.5 mM and about 100 mM, between about 0.5 mM and about 50 mM, between about 0.5 mM and about 10 mM, between about 0.5 mM and about 7 mM, or between about 1 mM and about 6 mM, between about 1.5 mM and about 5 mM, between about 2 mM and about 4 mM, or between about 2.5 mM and about 3.5 mM.

The methods may further comprise administering fluoride to the subject. In various embodiments, the fluoride may be present in the formulation at between about between about 50 parts per million (ppm) and about 20,000 ppm, between about 50 ppm and about 10,000 ppm, between about 50 ppm and about 5000 ppm, between about 50 ppm and about 1000 ppm, between about 50 ppm and about 500 ppm, or about 75 ppm and about 400 ppm, between about 100 ppm and about 300 ppm, between about 150 ppm and about 250 ppm, or about 200 ppm.

In other embodiments, the polypeptides and any ion sources and/or fluoride are administered in a formulation, and the formulation may be, but is not limited to, toothpaste, toothpowders, mouthwash, gel, dental floss, liquid dentifrices, dental tablets, topical gels, troches, chewing gums, dental pastes, gingival massage creams, gargle tablets, lozenges, tooth trays, tooth varnishes, and food products. In specific embodiments, the formulation may comprise a lozenge, a gel, or mouthwash.

In other embodiments, the polypeptide is administered in a formulation and is present in the formulation at a concentration of between about 0.01 mM and about 0.5M, or between about 0.01 mM and about 0.1M, between about 0.01 mM and about 50 mM, between about 0.01 mM to about 20 mM, or between about 0.1 mM to about 15 mM, or between about 0.5 mM to about 12.5 mM, or between about 0.8 mM and about 10 mM.

In one embodiment, the subject is one suffering from demineralization of enamel, typically characterized as incipient carious lesions, of one or more tooth. In other embodiments, the subject has an incipient carious lesion, tooth hypersensitivity, and/or white spot lesion (a clinical condition that is a result of demineralization of enamel), and the effective amount is an amount that is effective to treat the incipient carious lesions, tooth hypersensitivity, and/or white spot lesion.

In a further aspect, the invention provides polypeptide consisting of the amino acid sequence of (SYENSHSQAINVDRT)$_{1-10}$; (shADP5; SEQ ID NO: 16)

or (SYEKSHSQAINTDRT)$_{1-10}$. (sADP5; SEQ ID NO: 24)

In another aspect, the invention provides oral care products, comprising (a) (SYENSHSQAINVDRT)$_{1-10}$ (shADP5; SEQ ID NO:16); and/or (SYEKSHSQAINTDRT)$_{1-10}$ (sADP5; SEQ ID NO:24);

(b) at least one calcium ion source, and (c) at least one phosphate ion source.

In various embodiments, the calcium ion source may be selected from the group consisting of calcium acetate, calcium carbonate, calcium citrate, calcium chloride, calcium gluconate, calcium glycerophosphate, calcium lactate, and calcium phosphate. In various further embodiments, the phosphate ion source is selected from the group consisting of aluminum phosphates, calcium phosphates, potassium phosphates, and sodium phosphates. In various further embodiments, the oral care product has (i) a $Ca^{2+}$ concentration ranging between about 1 mM and about 2 M, or between about 1 mM and about 1M, between about 1 mM and about 0.5M, between about 1 mM and about 100 mM, between about 1 mM and about 50 mM, between about 1 mM and about 10 mM, between about 2 mM and about 8 mM, between about 3 mM and about 7 mM, between about 4 mM and about 6 mM, or between about 4.5 mM and about 5.5 mM; and (ii) a $PO_4^{3-}$ concentration ranging between about 0.5 mM and about 2 M, or between about 0.5 mM and about 1M, between about 0.5 mM and about 0.5M, between about 0.5 mM and about 100 mM, between about 0.5 mM and about 50 mM, between about 0.5 mM and about 10 mM, between about 0.5 mM and about 7 mM, or between about 1 mM and about 6 mM, between about 1.5 mM and about 5 mM, between about 2 mM and about 4 mM, or between about 2.5 mM and about 3.5 mM.

In a further embodiment, the oral care product may further comprise fluoride. In various non-limiting embodiments, the fluoride may be present in the oral care product at between about between about 50 parts per million (ppm) and about 20,000 ppm, between about 50 ppm and about 10,000 ppm, between about 50 ppm and about 5000 ppm, between about 50 ppm and about 1000 ppm, between about 50 ppm and about 500 ppm, or about 75 ppm and about 400 ppm, between about 100 ppm and about 300 ppm, between about 150 ppm and about 250 ppm, or about 200 ppm.

In various embodiments, the oral care product may be selected from the group consisting of toothpaste, toothpowders, mouthwash, gel, dental floss, liquid dentifrices, dental tablets, topical gels, troches, chewing gums, dental pastes, gingival massage creams, gargle tablets, lozenges, tooth trays, tooth varnishes, and food products. In specific embodiments, the oral care product comprises a lozenge a gel, or mouthwash.

In other embodiments, the polypeptide may be present in the pharmaceutical composition at a concentration of between about 0.01 mM and about 0.5M, or between about 0.01 mM and about 0.1M, between about 0.01 mM and about 50 mM, between about 0.01 mM to about 20 mM, or between about 0.1 mM to about 15 mM, or between about 0.5 mM to about 12.5 mM, or between about 0.8 mM and about 10 mM.

BRIEF DESCRIPTION OF THE DRAWINGS

The foregoing aspects and many of the attendant advantages of the described technology will become more readily appreciated as the same become better understood by reference to the following detailed description, when taken in conjunction with the accompanying drawings, wherein:

FIG. 2(a) shows one half of a sectioned tooth after the staining. FIGS. 2(b), (c) and (d) show different views of the left quarter of the tooth that was sectioned from the half tooth. FIGS. 2(e), (f) and (g) show different views of the right quarter of the tooth that was sectioned from the half tooth.

DETAILED DESCRIPTION

Figure 1:
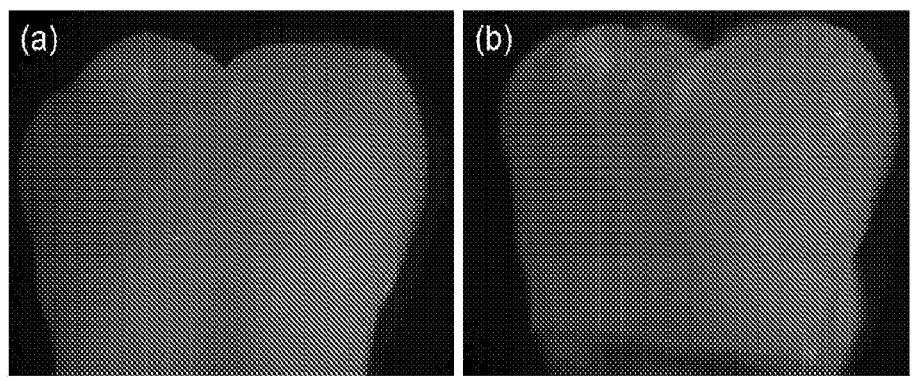
FIG. 1 depicts a tooth (a) before and (b) after sectioning vertically as described in Example 2.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual* of *Basic Technique*, 2<sup>nd</sup> Ed. (R. I. Freshney. 1987. Liss, Inc. New York, N.Y.), *Gene Transfer and Expression Protocols, pp.* 109-128, ed. E. J. Murray, The Humana Press Inc., Clifton, N.J.), and the Ambion 1998 Catalog (Ambion, Austin, Tex.).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term, or may mean plus or minus 10% of the particular term.

As used herein, the singular forms "a", "an" and "the" include plural referents unless the context clearly dictates otherwise. "And" as used herein is interchangeably used with "or" unless expressly stated otherwise. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (for example, "such as") provided herein, is intended merely to better illuminate the embodiments and does not pose a limitation on the scope of the claims unless otherwise stated. No language in the specification should be construed as indicating any non-claimed element as essential.

All embodiments of any aspect of the described technologies can be used in combination, unless the context clearly dictates otherwise.

In a first aspect, methods for whitening teeth or for mineralizing teeth, are provided, comprising administering to a subject in need thereof an amount effective to whiten teeth or to mineralize teeth of a biomineralizing polypeptide or pharmaceutical composition or oral care product of any embodiment or combination of embodiments of the technologies. The methods can further comprise administering at least one calcium ion source and at least one phosphate ion source to the subject. The calcium ion source and phosphate ion source can be co-administered or serially administered. The calcium ion source and phosphate ion source can be administered before the biomineralizing polypeptide, concurrently with the biomineralizing polypeptide, or after the biomineralizing polypeptide.

As shown herein, the inventors have discovered that biomineralizing polypeptides can be used to whiten teeth and to remineralize tooth enamel. While not being bound by a specific mechanism of action, the inventors believe that the polypeptides direct mineralization of dental lesions to form a "dento-mimetic" mineral layer, which also serves to reduce dental hypersensitivity and bacterial infiltration. It is further believed that some of the polypeptides exert their activity via binding to hydroxyapatite (HA) surfaces on the tooth to kinetically promote re-mineralization, occluding of dentin tubules to prevent/limit stimulants from reaching the tubules, and/or rebuilding lost mineral to create a physical barrier against bacteria. The inventors further demonstrate that crystalline mineral layer can be formed on enamel lesions in the presence of $Ca^{2+}$ and $PO_4^{3-}$ ions together with polypeptides of the invention under physiologically viable conditions. The inventors also demonstrate that the methods can promote layer-by-layer mineralization, i.e., more layers as the treatment is applied showing that the number of layers increases. The inventors further demonstrate that use of the polypeptides of the invention allow the delivery and incorporation of fluoride ions into the remineralized layer even at F concentrations much lower than those used in current dental practice and products. Thus, the invention provides a great improvement over previously reported methods for treating dental disease.

The methods of the present application have a number of attendant advantages. The described methods clear stains present on tooth surfaces in addition to re-mineralizing tooth surfaces. Without clearing stains any re-mineralization would create incipient lesions on the tooth. The described methods lead to whitened and smooth tooth surfaces in contrast to conventional whiteners which may lead to uneven tooth surfaces, with "hills" and "valleys".

As used herein, a "biomineralizing polypeptide" is any polypeptide capable of generating a hydroxyapatite layer on a tooth in the presence of calcium ions and phosphate ions. Several biomineralizing polypeptides are described in PCT application No. PCT/US2012/039650, which is incorporated herein by reference in its entirety. The calcium ions are present due to at least one calcium ion source. The calcium ion source can generally be any calcium salt. Illustrative calcium ion sources include, but are not limited to, calcium acetate, calcium carbonate, calcium citrate, calcium chloride, calcium gluconate, calcium glycerophosphate, calcium lactate, and calcium phosphate. In some cases, combinations of more than one calcium ion source may be used. In some embodiments, the calcium ion source is not calcium phosphate. The phosphate ions are present due to at least one phosphate ion source. The phosphate ion source can generally be any phosphate salt. Illustrative phosphate ion sources include, but are not limited to, aluminum phosphates, calcium phosphates, potassium phosphates, and sodium phosphates. Calcium phosphates include monocalcium phosphate, dicalcium phosphate, and tricalcium phosphate. Potassium phosphates include monopotassium phosphate, dipotassium phosphate, and tripotassium phosphate. Sodium phosphates include sodium dihydrogen phosphate, sodium hydrogen phosphate, and trisodium phosphate. In some cases, combinations of more than one phosphate ion source may be used. In some embodiments, the phosphate ion source is not calcium phosphate. The concentration of calcium ions can generally be any concentration, such as about 0.1 mM to about 100 mM. In various further embodiments, the calcium ions are used at a concentration of between about 1 mM and about 2 M, or between about 1 mM and about 1M, between about 1 mM and about 0.5M, between about 1 mM and about 100 mM, between about 1 mM and about 50 mM, between about 1 mM and about 10 mM, between about 2 mM and about 8 mM, between about 3 mM and about 7 mM, between about 4 mM and about 6 mM, or between about 4.5 mM and about 5.5 mM. In various further embodiments, the phosphate ions are used at a concentration ranging between about 0.5 mM and about 2 M, or between about 0.5 mM and about 1M, between about 0.5 mM and about 0.5M, between about 0.5 mM and about 100 mM, between about 0.5 mM and about 50 mM, between about 0.5 mM and about 10 mM, between about 0.5 mM and about 7 mM, or between about 1 mM and about 6 mM, between about 1.5 mM and about 5 mM, between about 2 mM and about 4 mM, or between about 2.5 mM and about 3.5 mM. The ratio of calcium ions to phosphate ions can generally be any ratio, such as about 5:3. In various embodiments, higher ionic concentrations may be used when gel formulations are employed (in non-limiting embodiments, 0.1 M or more), while lower ionic concentrations may be used when solution formulations are employed (in non-limiting embodiments, 50 mM or less).

In some embodiments, biomineralizing polypeptides comprise or consist of one or more amelogenin derived polypeptides (ADPs).

In one embodiment, biomineralizing polypeptides comprise or consist of (WP(A/S)TDKTKREEVD)$_{1-10}$;  (ADP3; SEQ ID NO: 7)

(PGYIN(L/F)SYE(K/N)SHSQAIN(T/V)DRTA)$_{1-10}$;  (ADP5; SEQ ID NO: 13)

(LPPLFSMPLSPILPELPLEAWPAT)$_{1-10}$;  (ADP6; SEQ ID NO: 17)

(HPP(S/T)HTLQPHHH(L/I)PVVPAQQPV(A/I)PQQPMMPVPG(H/Q)HSMTP(T/I)QH)$_{1-10}$;  (ADP7; SEQ ID NO: 18)

(SYENSHSQAINVDRT)$_{1-10}$;  (shADP5; SEQ ID NO: 16)

(SYEKSHSQAINTDRT)$_{1-10}$;  (sADP5; SEQ ID NO: 24)
and 12-42 contiguous amino acids of
(HPP(S/T)HTLQPHHH(L/I)PVVPAQQPV(A/I)PQQPMMPVPG(H/Q)HSMTP(T/I)QH)$_{1-10}$;  (ADP7; SEQ ID NO: 18)

or functional equivalents thereof. In various embodiments, the recited polypeptides may be present in 1, 2, 3, 4, 5, 6, 7, 8, 9, or 10 copies, or ranges such as 2-10. For example, a tetrapeptide can be used that contains four consecutive copies of ADP6. In some embodiments, the biomineralizing polypeptides comprise or consist of two or more of the ADPs or functional equivalents thereof. In some embodiments, the biomineralizing polypeptides comprise one or more fusion peptides comprising or consisting of two or more of the ADPs or functional equivalents thereof.

As used herein, a "functional equivalent" of a polypeptide is one that retains the biological activity of the polypeptide in treating dental disease, and includes one or more amino acid substitutions, deletions, additions, or insertions. In various embodiments, the functional equivalent is at least 50%, 55%, 60%, 65%, 70%, 75%, 80%, 85%, 90%, 91%, 92%, 93%, 94%, 95%, or more identical to the recited polypeptide. In some embodiments, the functional equivalent is a shortened version of an ADP described herein.

In another aspect, the invention provides a polypeptide consisting of the amino acid sequence of (SYENSHSQAINVDRT)1-10;  (shADP5; SEQ ID NO: 16)
or
(SYEKSHSQAINTDRT)1-10.  (sADP5; SEQ ID NO: 24)

The inventors have discovered that these polypeptides of the invention have significantly enhanced aqueous solubility compared to other ADP5 polypeptides described to date, while retaining the mineralization directing properties of ADP5. Thus, the polypeptides of this aspect of the invention provide a significant improvement over previous biomineralization peptides. The polypeptide may be present in 1, 2, 3, 4, 5, 6, 7, 8, 9, or 10 copies; in one specific embodiment, the polypeptide is present in one copy. While the polypeptides consist of the recited amino acid sequence, the invention further provides fusion proteins comprising a polypeptide of this aspect of the invention fused to another polypeptide, formulations comprising the polypeptides of this aspect of the invention and one or more calcium and/or phosphate ion sources, and various oral care products comprising the polypeptides of this aspect of the invention, as described herein.

As used throughout the present application, the term "polypeptide" is used in its broadest sense to refer to a sequence of subunit amino acids, whether naturally occurring or of synthetic origin. The polypeptides may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, or glycosylation. Such linkage can be covalent or non-covalent as is understood by those of skill in the art.

In one embodiment, the methods comprise administering a polypeptide comprising or consisting of the amino acid sequence (PGYIN(L/F)SYE(K/N)SHSQAIN(T/V)DRTA)$_{1-10}$ (ADP5; SEQ ID NO:13), or a functional equivalent thereof. In an alternative embodiment, ADP5 comprises or consists of (PGYINFSYENSHSQAINVDRTA)$_{1-10}$ (ADP5H; SEQ ID NO:15), or a functional equivalent thereof. In another alternative embodiment, ADP5 comprises or consists of (PGYINLSYEKSHSQAINTDRTA)$_{1-10}$ (ADP5M; SEQ ID NO:14), or a functional equivalent thereof. In yet another alternative embodiment, ADP5 comprises or consists of (SYENSHSQAINVDRT)$_{1-10}$ (shADP5; SEQ ID NO:16), or a functional equivalent thereof. In an alternative embodiment, ADP5 comprises or consists of (SYEKSHSQAINTDRT)$_{1-10}$ (sADP5; SEQ ID NO:24) or a functional equivalent thereof. In various embodiments, ADP5, ADP5M, shADP5, sADP5, or ADP5H is present in 1, 2, 3, 4, 5, 6, 7, 8, 9, or 10 copies, or ranges such as 2-10. In an alternative embodiment, ADP5, ADP5M, shADP5, sADP5, or ADP5H is present in 1 copy. In yet another alternative embodiment, the ADP5 comprises or consists of ADP5H or shADP5, preferably in one copy. In yet another alternative embodiment, the ADP5 comprises or consists of sADP5, preferably in one copy. In some embodiments, the biomineralizing polypeptides comprise or consist of two or more of the ADPs or functional equivalents thereof. In some embodiments, the biomineralizing polypeptides comprise one or more fusion peptides comprising or consisting of two or more of the ADPs or functional equivalents thereof.

In another embodiment, the methods comprise administering a polypeptide comprising or consisting of the amino acid sequence: (HPP(S/T)HTLQPHHH(L/I)PVVPAQQPV(A/I)PQQPMMPVPG(H/Q)HSMTP(T/I)QH)$_{1-10}$ (ADP7; SEQ ID NO:18), or a functional equivalent thereof. In an embodiment, the ADP7 comprises or consists of (HPPSHTLQPHHHLPVVPAQQPVAPQQPMMPVPGHHSMTPTQH)$_{1-10}$ (ADP7M; SEQ ID NO:19); (HPPTHTLQPHHHIPVVPAQQPVIPQQPMMPVPGQHSMTPIQH)$_{1-10}$ (ADP7H; SEQ ID NO:20), or a functional equivalent thereof. In various embodiments, ADP 7, ADP7M, or ADP7H is present in 1, 2, 3, 4, 5, 6, 7, 8, 9, or 10 copies, or ranges such as 2-10. In an embodiment, ADP7, ADP7M, or ADPH7 is present in 1 copy. In another embodiment, the ADP7 comprises or consists of ADP7H in one copy. In some embodiments, the biomineralizing polypeptides comprise or consist of two or more of the ADPs or functional equivalents thereof. In some embodiments, the biomineralizing polypeptides comprise one or more fusion peptides comprising or consisting of two or more of the ADPs or functional equivalents thereof.

In a further embodiment, the polypeptide for use in the methods comprises or consists of the amino acid sequence WP(A/S)TDKTKREEVD)$_{1-10}$ (ADP3; SEQ ID NO:7), or a functional equivalent thereof. In an embodiment, ADP3 comprises or consists of ((WPATDKTKREEVD)$_{1-10}$ (ADP3M; SEQ ID NO:8) or (WPSTDKTKREEVD)$_{1-10}$ (ADP3H; SEQ ID NO:9), or a functional equivalent thereof. In various embodiments, ADP3, ADP3M, or ADP3H is present in 1, 2, 3, 4, 5, 6, 7, 8, 9, or 10 copies, or ranges such as 2-10. In an embodiment, ADP3, ADP3M, or ADP3H is present in 1 copy. In another embodiment, the ADP3 comprises or consists of ADP3H in one copy. In some embodiments, the biomineralizing polypeptides comprise or consist of two or more of the ADPs or functional equivalents thereof. In some embodiments, the biomineralizing polypeptides comprise one or more fusion peptides comprising or consisting of two or more of the ADPs or functional equivalents thereof.

In various further embodiments, the polypeptide for use in the methods comprises or consists of a polypeptide selected from the group consisting of selected from the group consisting of:

(HTLQPHHH(L/I)PVV)$_{1-10}$; (ADP1; SEQ ID NO: 1)

(VPG(H/Q)HSMTP(T/I)QH)$_{1-10}$; (ADP2; SEQ ID NO: 4)

(HPP(S/T)HTLQPHHH(L/I)PVV)$_{1-10}$; (ADP4; SEQ ID NO: 10)

(PAQQPV(A/I)PQQPMMP)$_{1-10}$; (ADP8; SEQ ID NO: 21)

(HTLQPHHHLPVV)$_{1-10}$; (ADP1M; SEQ ID NO: 2)

(HTLQPHHHIPVV)$_{1-10}$; (ADP1H; SEQ ID NO: 3)

(VPGHHSMTPTQH)$_{1-10}$; (ADP2M; SEQ ID NO: 5)

(VPGQHSMTPIQH)$_{1-10}$; (ADP2H; SEQ ID NO: 6)

(HPPSHTLQPHHHLPVV)$_{1-10}$; (ADP4M; SEQ ID NO: 11)

(HPPTHTLQPHHHIPVV)$_{1-10}$; (ADP4H; SEQ ID NO: 12)

(PAQQPVAPQQPMMP)$_{1-10}$; (ADP8M; SEQ ID NO: 22)
and (PAQQPVIPQQPMMP)$_{1-10}$; (ADP8H; SEQ ID NO: 23)

or functional equivalents thereof.

In various embodiments, the recited polypeptides may be present in 1, 2, 3, 4, 5, 6, 7, 8, 9, or 10 copies, or ranges such as 2-10. In some embodiments, when present in more than one copy, the copies are contiguous to each other. In some embodiments, the polypeptide for use in the methods comprises a fusion of two or more of the ADPs described herein or functional equivalents thereof.

Each ADP and functional equivalent thereof has its own distinct kinetic profile and may exhibit a fast or slow kinetic profile. For example, ADP5 has a fast kinetic profile whereas ADP7 has a slow kinetic profile. In some embodiments, the biomineralizing polypeptide comprises or consists of at least one ADP with a slow kinetic profile and at least one ADP with a fast kinetic profile. In some embodiments, the biomineralizing polypeptide only comprises or consists of one or more ADPs with fast kinetic profiles. In some embodiments, the biomineralizing polypeptide only comprises or consists of one or more ADPs with slow kinetic profiles. Fast kinetics refers to fast mineral formation, such as immediate mineral formation, while slow mineral formation refers to mineral formation over a period of time, such as about 5 minutes to about 1 hour. In some embodiments, a first biomineralizing peptide having faster kinetics can be used in combination with a second biomineralizing peptide having slower kinetics.

In some embodiments, the polypeptides of the invention or the polypeptide for use in the methods further comprises at least one fluorescent agent. In some embodiments, the polypeptides of the invention or the polypeptide for use in the methods comprises a polypeptide covalently linked to at least one fluorescent agent. Illustrative fluorescent agents include, but are not limited to, fluorescein, 6-FAM, rhodamine, Texas Red, California Red, iFluor594, tetramethylrhodamine, a carboxyrhodamine, carboxyrhodamine 6F, carboxyrhodol, carboxyrhodamine 110, Cascade Blue, Cascade Yellow, coumarin, Cy2®, Cy3®, Cy3.5®, Cy5®, Cy5.5®, Cy70®, Cy-Chrome, DyLight® 350, DyLight® 405, DyLight® 488, DyLight® 549, DyLight® 594, DyLight® 633, DyLight® 649, DyLight® 680, DyLight® 750, DyLight® 800, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and -6-)-carboxy-X-rhodamine), HEX, Lucifer Yellow, Marina Blue, Oregon Green 488, Oregon Green 500, Oregon Green 514, Alexa Fluor® 350, Alex Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br2, BODIPY® 530/550, BODIPY® 558/568, BODIPY® 630/650, BODIPY® 650/665, BODIPY® R6G, BODIPY® TMR, BODIPY® TR, and combinations thereof.

The subject may be any subject whose teeth could be whitened or remineralized, including but not limited to mammals. In various embodiments, the mammal is a human, dog, cat, horse, cow, sheep, goat, pig, or other pet or food/dairy animal. In one embodiment, the subject is a human. In one embodiment, the subject is suffering from demineralization of enamel and/or dentin of one or more tooth. For example, the subject may have one or more of incipient carious lesion, tooth hypersensitivity, and/or white spot lesion, and the effective amount administered is an amount of the polypeptide and ions of Ca and $PO_4$ that is effective to treat the one or more incipient carious lesion, tooth hypersensitivity, and/or white spot lesion.

As used herein, "tooth whitening" and "dental bleaching" have identical meanings and can be used interchangeably. Tooth whitening and dental bleaching refer to decreasing the amount of chromagens or discolorants present in or on a tooth. In certain embodiments, tooth whitening refers to restoring a tooth to its original color. In certain other embodiments, dental bleaching refers to whitening a tooth beyond its natural, original color. Tooth whitening may be measured using methods known to those skilled in the art. In some embodiments, tooth whitening is measured using comparative shade guides. In some embodiments, tooth color and tooth whitening are measured using a colorimeter, such as a tristimulus colorimeter. Such instruments can be used to measure the color of the specimen (tooth) surface quantitatively. The CIE "L*a*b*" color system is commonly used in the commercial and scientific literature for quantitatively measuring teeth color (See Yiming, *J. Esther Restor. Dent.*, 15: 533-541 (2003)). The system uses one luminance parameter and two color coordinates to specify a point on a chromaticity diagram. The "L" value corresponds to lightness, the "a" value corresponds to red-green, and the "b" value corresponds to yellow-blue. A change in the color of a treated tooth can be calculated as $\Delta E_{Lab}=((\Delta L^*)^2+(\Delta a^*)^2+(\Delta b^*)^2)^{1/2}$. The value can generally be any value, and in some cases have a minimum value limited only by the detection limit of the instrument used to take the measurements.

As used herein, "mineralizing" or "remineralizing" are used interchangeably, and mean mineral layer formation on damaged enamel. Thus, subjects in need of mineralization are those that have damage to the enamel that can benefit from the mineralization methods of the invention. The methods may result in any amount of mineralization, as any such mineralization provides a therapeutic benefit to the subject. In various embodiments the mineralization may result in production of a mineral layer at least 1 μm on the tooth enamel; in other embodiments, the methods result in production of a mineral layer at least 2, 3, 4, 5, 6, 7, 8, 9, or 10 μm on the tooth enamel. In one embodiment, the mineral layer produced on the enamel comprises a dense mineralized layer containing hydroxyapatite, also known as hydroxyl apatite (Hap). In other embodiments, the newly formed mineral layer is integrated with the underlying enamel.

As used herein, unless otherwise described, an "amount effective" or "effective amount" refers to an amount of the polypeptide that is effective for whitening teeth and/or for mineralizing teeth. In some embodiments, the "amount effective" or "effective amount" means a concentration of about 0.01 mM to about 1 mM of the polypeptide. This includes a concentration of about 0.05 mM to about 0.5 mM or about 0.1 mM to about 0.5 mM. In some embodiments, the concentration is about 0.01, 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1 mM, including increments therein, of polypeptide. In a clinical setting, higher concentrations of polypeptide (for example, about 0.6 mM to about 0.8 mM) may be used. In a home use setting, lower concentrations of polypeptide (for example, about 0.01 mM to about 0.1 mM) may be used. In one embodiment, the polypeptide is administered in a formulation and is present in the formulation at a concentration of about 0.01 mM to about 20 mM; in various further embodiments, the polypeptide is present in the formulation at between about 0.01 mM and about 0.5M, or between about 0.01 mM and about 0.1M, between about 0.01 mM and about 50 mM, between about 0.01 mM to about 20 mM, or between about 0.1 mM to about 15 mM, or between about 0.5 mM to about 12.5 mM, or between about 0.8 mM and about 10 mM. In some embodiments, the "amount effective" or "effective amount" refers to an amount of a composition comprising the polypeptide that is effective for whitening teeth and/or for mineralizing teeth.

The methods may further comprise administering fluoride to the subject. In various embodiments, the fluoride may be present in the formulation at between about 50 ppm and about 20,000 ppm, or between about 50 ppm and about 10,000 ppm, between about 50 ppm and about 5000 ppm, between about 50 ppm and about 1000 ppm, between about 50 ppm and about 500 ppm, or about 75 ppm and about 400 ppm, between about 100 ppm and about 300 ppm, between about 150 ppm and about 250 ppm, or about 200 ppm. The examples demonstrate that use of the polypeptides of the invention allow the delivery and incorporation of fluoride ions into the remineralized layer even at fluoride concentrations much lower than those used in current dental practice and products.

The polypeptides are typically formulated as a pharmaceutical composition, such as those disclosed herein, and can be administered via any suitable route, including orally, parentally, by inhalation spray, or topically in dosage unit formulations containing conventional pharmaceutically acceptable carriers, adjuvants, and vehicles. In an embodiment, the pharmaceutical compositions and formulations are topically administration, such as in the form of ointments, lotions, creams, pastes, gels, drops, sprays, liquids and powders. Conventional pharmaceutical carriers, aqueous, powder or oily bases, thickeners and the like may be included.

In certain preferred embodiments, the polypeptides are delivered by: placing the polypeptides in contact with a tooth surface and applying a light source to the tooth. Without being bound by theory, it is believed that a light source can increase the rate of tooth whitening and/or for mineralizing. Such light sources can include diode lasers, PAC lights, and halogen lights.

In certain preferred embodiments, the polypeptides are delivered by placing the polypeptides in contact with a tooth surface also in the presence of at least one cleaning agent. Examples of cleaning agents include hydrogen peroxide, carbamide peroxide, titanium dioxide, nano-hydroxyapatite particles, zirconia powder, and combinations thereof.

In certain preferred embodiments, the biomineralizing polypeptides are present in a gel or other pharmaceutical composition, as described herein, placed in a mouth guard and applied to the teeth of a subject overnight. Such repeated overnight application of biomineralizing polypeptides can have especially beneficial whitening and/or for mineralizing effects.

Similarly, the biomineralizing polypeptides described herein can be applied to the teeth of a subject as a mouthwash, toothpaste, or tooth varnish on a daily basis to similar effect.

In some embodiments, the pharmaceutical compositions used in the methods described herein comprise at least one biomineralizing polypeptide and a calcium ion source. In some embodiments, the pharmaceutical compositions used in the methods described herein comprise at least one biomineralizing polypeptide and a phosphate ion source. In some embodiments, the pharmaceutical compositions used in the methods described herein comprise at least one biomineralizing polypeptide, a calcium ion source, and a phosphate ion source.

Dosage regimens can be adjusted to provide the optimum desired response (for example, a therapeutic or prophylactic response). A suitable dosage range may, for instance, be about 0.1 μg/kg to about 100 mg/kg body weight; alternatively, it may be about 0.5 μg/kg to about 50 mg/kg; about 1 μg/kg to about 25 mg/kg, or about 5 μg/kg to about 10 mg/kg body weight. The polypeptides can be delivered in a single bolus, or may be administered more than once (for example, 2, 3, 4, 5, or more times) as determined by an attending physician.

In various other embodiments, the heterologous polypeptide provides added functionality, for example, when the fusion polypeptides are used to whiten and/or mineralize teeth. Exemplary such heterologous polypeptides include, but are not limited to biomineralization-promoting polypeptides (that is, any other polypeptides that are useful for controlling or promoting biomineralization). As will be understood by those of skill in the art, the recited heterologous polypeptide may comprise or consist of the full length protein, or functional polypeptides derived therefrom. Such heterologous polypeptides are known to those of skill in the art. A recombinant fusion protein can comprise the ADP polypeptide and at least one heterologous polypeptide.

In a further aspect, pharmaceutical compositions are provided, comprising one or more polypeptides, recombinant fusion proteins, or compositions with a pharmaceutically acceptable carrier. The pharmaceutical compositions can be used, for example, in the methods described herein. The pharmaceutical composition may comprise in addition to the polypeptide (a) at least one lyoprotectant; (b) at least one surfactant; (c) at least one bulking agent; (d) at least one tonicity adjusting agent; (e) at least one stabilizer; (f) at least one preservative; and/or (g) at least one buffer.

In some embodiments, the buffer in the pharmaceutical composition is a Tris buffer, a histidine buffer, a phosphate buffer, a citrate buffer, or an acetate buffer. The pharmaceutical composition may also include at least one lyoprotectant, for example, sucrose, sorbitol, or trehalose. In certain embodiments, the pharmaceutical composition includes at least one preservative, for example, benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, or various mixtures thereof. In other embodiments, the pharmaceutical composition includes at least one bulking agent, such as glycine. In yet other embodiments, the pharmaceutical composition includes at least one surfactant, for example, polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or any combination thereof. The pharmaceutical composition may also include at least one tonicity adjusting agent, for example, a compound that renders the formulation substantially isotonic or isoosmotic with human blood. Exemplary tonicity adjusting agents include sucrose, sorbitol, glycine, methionine, mannitol, dextrose, inositol, sodium chloride, arginine, and arginine hydrochloride. In other embodiments, the pharmaceutical composition additionally includes at least one stabilizer, for example, a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides may be the sole active agent in the pharmaceutical composition, or the composition may further comprise one or more other active agents suitable for an intended use, including but not limited to antimicrobial polypeptides (inhibiting bacterial infection), other biomineralization-promoting polypeptides (that is, any other polypeptides that are useful for controlling or promoting biomineralization), inorganic material-binding polypeptides, three-dimensional scaffold-forming polypeptides, collagen, chitosan, amphiphilic peptides, protein-binding polypeptides, enamelin-derived polypeptides, tuftelin-derived peptides, statherin-derived polypeptides, dentin-derived polypeptides, bone sialoprotein-derived polypeptides, osteocalcin-derived polypeptides, osteopontin-derived polypeptides, proteins with caries inhibitory activity, casein, and bone morphogenetic-derived polypeptides.

The pharmaceutical compositions described herein generally comprise a combination of a compound described herein and a pharmaceutically acceptable carrier, diluent, or excipient. Such compositions are substantially free of non-pharmaceutically acceptable components, that is, contain amounts of non-pharmaceutically acceptable components lower than permitted by regulatory requirements. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (for example, tablet, capsules, lozenges, and so on).

These compositions can be prepared in a manner well known in the pharmaceutical art, and can be administered by any suitable route. In an embodiment, the pharmaceutical compositions and formulations are designed for topical administration, and may include ointments, lotions, creams, pastes, gels, drops, sprays, liquids and powders. Conventional pharmaceutical carriers, aqueous, powder or oily bases, thickeners and the like may be necessary or desirable.

The pharmaceutical compositions can be in any suitable form, including but not limited to tablets, pills, powders, lozenges, sachets, cachets, elixirs, suspensions, emulsions, solutions, syrups, aerosols (as a solid or in a liquid medium), ointments containing, for example, up to about 10% by weight of the active compound, soft and hard gelatin capsules, sterile injectable solutions, and sterile packaged powders.

In certain embodiments, the pharmaceutical compositions comprise at least one cleaning agent in addition to the biomineralizing polypeptides. These cleaning agents can include hydrogen peroxide, carbamide peroxide, titanium dioxide, nano-hydroxyapatite particles, zirconia powder, or combinations thereof. The pharmaceutical compositions can also include abrasive agents, such as silica particles. In some embodiments, the pharmaceutical compositions further comprise a calcium ion source, a phosphate ion source, or both.

In one embodiment the pharmaceutical compositions are in the form of an oral care product, including but not limited to toothpaste, toothpowders, mouthwash, dental floss, liquid dentifrices, dental tablets, topical gels, troches, chewing gums, dental pastes, gingival massage creams, gargle tablets, lozenges, and food products. Thus, in another aspect, oral care products are provided, comprising any embodiment or combination of embodiments of the polypeptides, recombinant fusion proteins, and/or compositions. Such oral care products can be used, for example, in whitening and/or mineralizing teeth. In some embodiments, provided herein are oral care products comprising at least one biomineralizing polypeptide, at least one calcium ion source, at least one phosphate ion source, and at least one cleaning agent. The calcium ions are present due to at least one calcium ion source. The calcium ion source can generally be any calcium salt. Illustrative calcium ion sources include, but are not limited to, calcium acetate, calcium carbonate, calcium citrate, calcium chloride, calcium gluconate, calcium glycerophosphate, calcium lactate, and calcium phosphate. In some cases, combinations of more than one calcium ion source may be used. In some embodiments, the calcium ion source is not calcium phosphate. The phosphate ions are present due to at least one phosphate ion source. The phosphate ion source can generally be any phosphate salt. Illustrative phosphate ion sources include, but are not limited to, aluminum phosphates, calcium phosphates, potassium phosphates, and sodium phosphates. Calcium phosphates include monocalcium phosphate, dicalcium phosphate, and tricalcium phosphate. Potassium phosphates include monopotassium phosphate, dipotassium phosphate, and tripotassium phosphate. Sodium phosphates include sodium dihydrogen phosphate, sodium hydrogen phosphate, and trisodium phosphate. In some cases, combinations of more than one phosphate ion source may be used. In some embodiments, the phosphate ion source is not calcium phosphate. The concentration of calcium ions can generally be any concentration, such as about 0.1 mM to about 100 mM. In various further embodiments, the calcium ions are used at a concentration of between about 1 mM and about 2 M, or between about 1 mM and about 1M, between about 1 mM and about 0.5M, between about 1 mM and about 100 mM, between about 1 mM and about 50 mM, between about 1 mM and about 10 mM, between about 2 mM and about 8 mM, between about 3 mM and about 7 mM, between about 4 mM and about 6 mM, or between about 4.5 mM and about 5.5 mM. The concentration of phosphate ions can generally be any concentration, in the range of 0.5 mM and about 2 M. In various further embodiments, the phosphate ions are used at a concentration ranging between about 0.5 mM and about 2 M, or between about 0.5 mM and about 1M, between about 0.5 mM and about 0.5M, between about 0.5 mM and about 100 mM, between about 0.5 mM and about 50 mM, between about 0.5 mM and about 10 mM, between about 0.5 mM and about 7 mM, or between about 1 mM and about 6 mM, between about 1.5 mM and about 5 mM, between about 2 mM and about 4 mM, or between about 2.5 mM and about 3.5 mM. The ratio of calcium ions to phosphate ions can generally be any ratio, such as about 5:3. In a further embodiment, the oral care product may further comprise fluoride. In various non-limiting embodiments, the fluoride may be present in the oral care product at between about between about 50 parts per million (ppm) and about 20,000 ppm, between about 50 ppm and about 10,000 ppm, between about 50 ppm and about 5000 ppm, between about 50 ppm and about 1000 ppm, between about 50 ppm and about 500 ppm, or about 75 ppm and about 400 ppm, between about 100 ppm and about 300 ppm, between about 150 ppm and about 250 ppm, or about 200 ppm. In further embodiments, the oral care products comprise at least one biomineralizing polypeptide, calcium, phosphate, and one or more of hydrogen peroxide, titanium dioxide, carbamide peroxide, nano-hydroxyapatite particles, and zirconia powder.

Several exemplary embodiments of the present application are summarized in Table 1 below.

TABLE 1

| Product Type | Formulation | Use area |
|---|---|---|
| Whitening gel with Fast mineralizing Polypeptides | Gel | In-clinic Power Bleaching |
| Whitening gel with Fast mineralizing Polypeptides & Laser light | Gel | In-clinic Power Bleaching |
| Whitening gel with Fast mineralizing Polypeptides & customized tray | Gel | In-clinic Power Bleaching |

TABLE 1-continued

| Product Type | Formulation | Use area |
|---|---|---|
| Whitening gel with Regular mineralizing Polypeptides & Laser light | Gel | At-home fast Bleaching |
| Whitening gel with Regular mineralizing Polypeptides & Laser light | Gel | At-home fast Bleaching |
| Whitening gel with Regular mineralizing Polypeptides & Tray | Gel | At-home fast Bleaching |
| Whitening toothpaste with Regular mineralizing Polypeptides | Toothpaste | At-home Daily Bleaching |
| Whitening toothpaste with Mild mineralizing Polypeptides | Toothpaste | At-home Daily Bleaching |
| Whitening toothpaste with Mild mineralizing Polypeptides & 2-3% $H_2O_2$ | Toothpaste | At-home Daily Bleaching |
| Whitening toothpaste with Mild mineralizing Polypeptides & 2-3% carbamide peroxide | Toothpaste | At-home Daily Bleaching |
| Whitening Toothpaste with Mild mineralizing Polypeptides | Toothpaste | At-home Daily Bleaching |
| Whitening solution with Mild mineralizing Polypeptides | Mouthwash | At-home Daily Bleaching |
| Whitening solution with Mild mineralizing Polypeptides & chimeric AMPs (separate) | Mouthwash | At-home Daily Bleaching |

As used in this table, "fast" refers to a rapid single shot whitening treatment, "regular" refers to a clinically viable chairside treatment time period, and "mild" refers to over the counter consumer products.

All of these aspects/embodiments disclosed herein can be combined with any other aspect/embodiment, unless the context clearly dictates otherwise.

EXAMPLES

Example 1. Polypeptide Synthesis rM180 amelogenin was created as described previously by Moradian-Oldak et al. (*J. Struct. Biol.*, 2000, 131(1):27-37). The ADPs were synthesized by standard solid phase peptide synthesis technique on Wang resin using Fmoc chemistry and HBTU activation. CSBio 336s (CSBio, Menlo Park, Calif., USA) automated peptide synthesizer was used for the synthesis. The resulting resin-bound polypeptides were cleaved and side-chain-deprotected using Reagent K (trifluoroacetic acid/thioanisole/$H_2O$/phenol/ethanedithiol (87.5:5:5:2.5)) and, precipitated by cold ether. The crude polypeptides obtained were purified by reverse phase high performance liquid chromatography up to a >98% purity (Gemini 10µ C18 110A column). The masses of the purified polypeptides were checked by mass spectroscopy using a MALDI-TOF mass spectrometer (Bruker Daltonics, Billerica, Mass., USA).

Example 2. Experimental In Vitro Procedures of Re-Mineralization Using the Peptide Solution on Rat Tooth Rat teeth (molars) were obtained from sacrificed rats (for example, Sprague Dawley rats, age 3 weeks or older) from animal facility, collected, and stored in 100% alcohol. Prior to the re-mineralization experiments the teeth were stored in 1% bleach for 24 hours. The teeth did not have soft tissues or plaque/tartar. The teeth were then dried in an incubator in air at 37° C. for 3-6 hours to produce dry surface. The root site and section the crown were removed vertically using a diamond blade. Pictures were taken with camera attached to optical microscope. Exposed dentine sites in the one half of the sectioned tooth were etched with 35% phosphoric acid (Ultraetch™) for 60 seconds (to facilitate the stain intake). The etching gel was removed by rinsing the sample with distilled water for 3 minutes. The staining solution was prepared by boiling 2 g of tea in 100 ml of deionized water for 5 minutes, and then cooled down to room temperature and filtered. The tooth sample was soaked in the staining solution and incubated at 37° C. at 150 rpm for 24 hours. The tooth was removed from the staining solution and sonicated for 30 seconds in deionized water (sonic bath) to remove the excess amount of tea particles attached to tooth extrinsically. The one half of the sectioned tooth was cut vertically into half again to form two quarter sections of the tooth. A second set of pictures were taken with camera attached to optical microscope. One of the quarter pieces was stored in 24 mM Tris Buffer (pH: 7.4) for control and the other one was used for in vitro re-mineralization. The portion used for in vitro re-mineralization was submerged into peptide solution (600 µl) containing a mineralization polypeptide in a 48 well plate and incubated for 10 minutes at 37° C. After incubation, the mineralized tooth was placed in a new well. 400 µl of 9.6 mM $CaCl_2$ and 400 µl of 5.6 mM $KH_2PO_4$ were added to the well and quickly mixed with a pipetting the solution up and down. The tooth was incubated in the mineralization solution for 16 hours at 37° C. The mineralization polypeptide was SYENSHSQAINVDRT (shADP5; SEQ ID NO:16). The quarter portion of the tooth which had been exposed to the polypeptide solution, calcium ion source and phosphate ion source was observed to be lighter in color than the control In certain experiments, mineralization was repeated with a fresh polypeptide and mineralization solution for the second round of re-mineralization.

Example 3. Experimental In Vitro Procedures of Re-mineralization Using the Peptide Solution on Human Tooth A caries-free human tooth was sterilized in 1% bleach solution for 24 hours then removed and vigorously rinsed with deionized water. The root site was removed and the crown sectioned vertically using a diamond blade. Pictures were taken with a camera attached to an optical microscope. FIG. 1(a) shows the original tooth before sectioning vertically. FIG. 1(b) shows one half of the original tooth that was sectioned.

Figure 2:
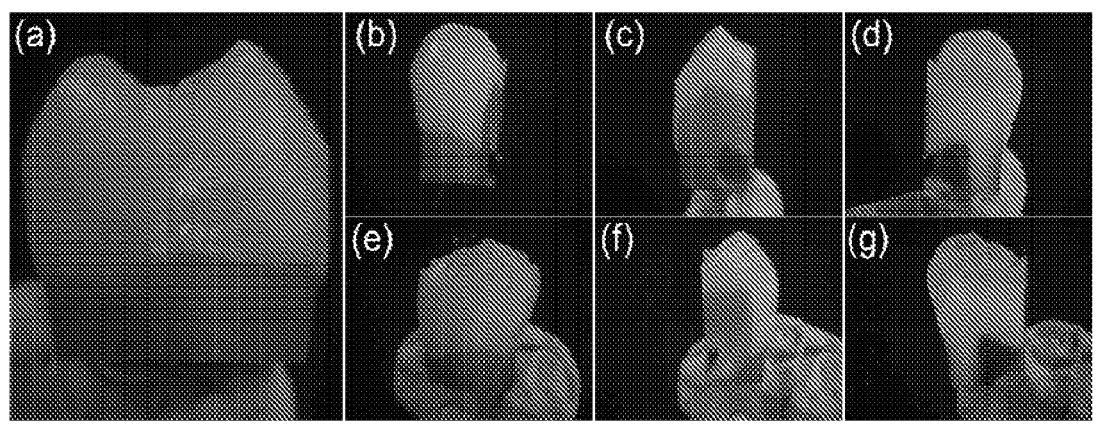
FIGS. 2(a) to 2(g) depict various sections of a tooth after staining as described in Example 2.
Figure 3:
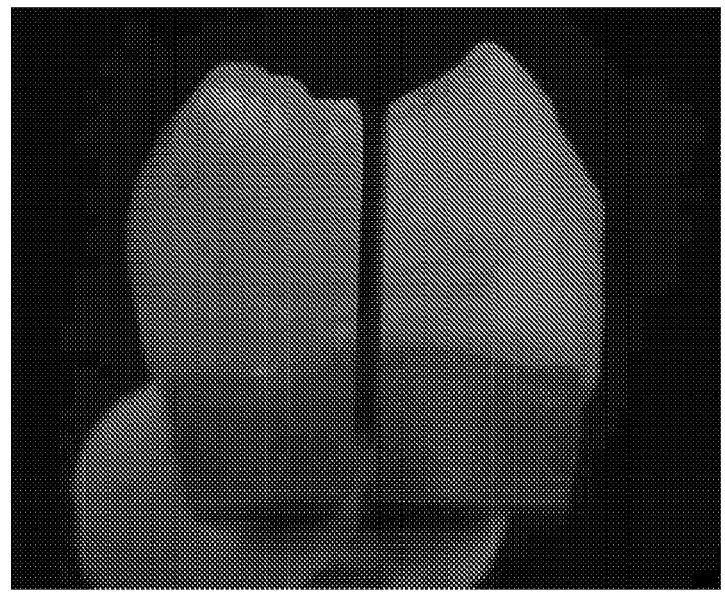
FIG. 3 shows the left quarter (control) and the right quarter of the tooth (test tooth) as described in Example 2.

The exposed dentine sites were etched with 35% phosphoric acid (Ultraetch™) for 60 seconds (to facilitate the stain intake). The etching gel was removed by rinsing the sample with distilled water for 3 minutes. The staining solution was prepared by boiling 2 g of tea in 100 ml of deionized water for 5 minutes, which was then cooled down to room temperature and filtered. The tooth was soaked in the staining solution and incubated at 37° C. at 150 rpm for 24 hours. The tooth was then removed from the staining solution and sonicated for 30 seconds in deionized water (sonic bath) to remove the excess amount of tea particles attached to tooth extrinsically. The sectioned tooth was cut vertically in half again to form two quarter sections of the tooth. FIGS. 2(a) to 2(g) show various sections of the tooth after the staining. FIG. 2(a) shows the one half of the sectioned tooth after the staining. Figures (b), (c) and (d) show different views of the left quarter of the tooth that was sectioned from the tooth. Figures (e), (0 and (g) show different views of the right quarter of the tooth that was sectioned from the tooth. As can be observed from FIGS. 2(a) to 2(g), brown stains from the staining solution were formed on the surface and below the surface of the tooth. The left quarter of the tooth was stored in 24 mM Tris Buffer (pH: 7.4) for control and the right quarter of the tooth (test tooth) was used for in vitro re-mineralization. The test tooth was submerged into peptide solution (600 µl) containing a mineralization polypeptide in a 48 well plate and incubated for 10 minutes at 37° C. After incubation, the tooth was removed and placed into to a new well. A mineralization solution of 400 µl of 9.6 mM $CaCl_2$ and 400 µl of 5.6 mM $KH_2PO_4$ was added and quickly mixed by pipetting the solution up and down. The test tooth was incubated in the mineralization solution for 16 hours at 37° C. The mineralization polypeptide used was SYENSHSQAINVDRT (shADP5; SEQ ID NO:16). FIG. 3 shows the left quarter (control) and the right quarter of the tooth (test tooth). As can be seen in FIG. 3, the right quarter which had been exposed to the polypeptide solution, calcium ion source and phosphate ion source appeared lighter in color than the left quarter (control). In certain experiments, mineralization was repeated with a fresh polypeptide and mineralization solution for the second round of re-mineralization.

Figure 4:
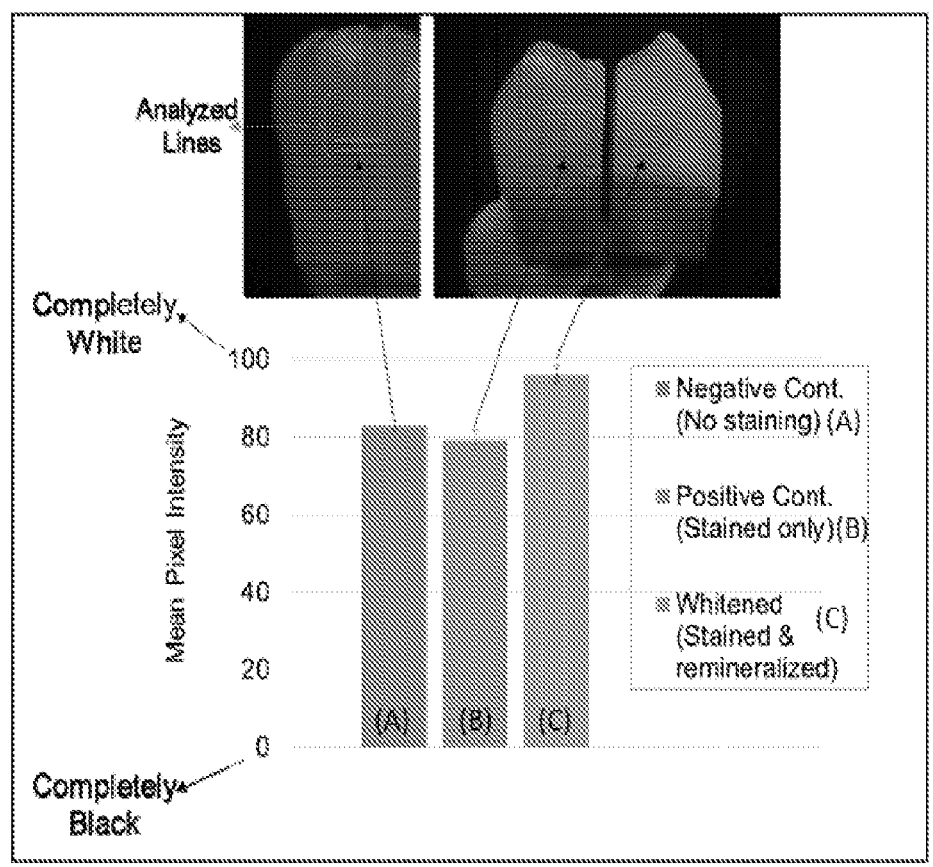
FIG. 4 depicts a line profile analysis of a portion of the original tooth (before staining), a portion of the tooth after staining, and a portion of tooth after staining and remineralization, as described in Example 2.

FIG. 4 shows a line profile analysis of a portion of the original tooth (before staining), a portion of the tooth after staining, and a portion of tooth after staining and remineralization. The bar chart in FIG. 4 shows the Mean Pixel Intensity (MPI) analyzed using ImageJ™ software on images of the tooth at before staining, after staining, and after staining and remineralization. A zero MPI indicates completely black while one hundred MPI indicates completely white. As can be observed from FIG. 4, the portion of the tooth that was stained and had subsequently undergone the remineralization treatment showed a higher MPI than the original tooth and the tooth after staining. Therefore, the remineralization treatment with the polypeptide solution and ion sources resulted in improved whiteness over the original tooth and the stained tooth.

Example 4. Mineralization Polypeptide Solution Formulation

An exemplary solution formulation of a mineralization polypeptide described herein consists of Tris buffer pH 7.4, $CaCl_2$ as the calcium ion source, $KH_2PO_4$ as the phosphate ion source, and the mineralization polypeptide.

Example 5. Mineralization Polypeptide Gel Formulation

An exemplary gel formulation of a mineralization polypeptide described herein is as in follows:

TABLE 2

| Ingredient | Weight % |
|---|---|
| Solvent: | |
| Aqueous 1.6 mM shADP5 polypeptide | 50 |
| Aqueous 960 mM $CaCl_2$ | |
| Aqueous 576 mM $KH_2PO_4$ or $K_2HPO_4$ | |

TABLE 2-continued

| Ingredient | Weight % |
|---|---|
| Preservative: | |
| Potassium sorbate | 0.5 |
| Thickener/humectant: | |
| Propylene glycol (PPG) | 3 |
| Glycerol (glycerin) | 15 |
| Cellulose Gum | 1 |
| Sweetener/flavor: | |
| sorbitol (60% aqueous solution) | 30 |
| Surfactant: | |
| simethicone (antifoam) | 0.5 |

Example 6. Mineralization Polypeptide Tablet Formulation

An exemplary tablet formulation of a mineralization polypeptide described herein is as follows:

TABLE 3

| Component | Weight (mg) |
|---|---|
| Active Ingredient: | |
| mineralization polypeptide, calcium ions, phosphate ions | 300 |
| Diluent: | |
| spray-dried lactose (SuperTab ® 11SD) | 88 |
| Lubricant: | |
| magnesium stearate | 6 |
| Glidant: | |
| talc | 6 |

Example 7. Solution Mineralization Approach

The root site of an extracted human tooth was removed and the crown portion of the tooth was sectioned vertically into half. A thin layer of enamel was removed from one half of the sectioned tooth such that the dentin layer is exposed without completely removing the enamel on the tooth. This allowed imaging of the enamel surfaces after the mineralization experiment without the problem of surface reflection, and provides a more parallel surface from which to compare the whiteness results. The sectioned tooth was fixed onto a glass slide with epoxy. Initial color measurements of each of the four sides of the sectioned tooth were obtained using a Minolta Chroma Meter CR-200 (Konica Minolta, Tokyo, Japan), according to manufacturer instructions, using a white background and a black background. The sectioned tooth was incubated in a mineralization polypeptide solution for 10 minutes at 37° C. and then in a solution with calcium ions and phosphate ions for 2 hours at 37° C. Color measurements of each of the four sides of the sample were taken as described initially. The sectioned was rinsed with deionized water and the remineralization process (incubation in polypeptide solution, incubation in solution of ion sources, and rinsing with deionized water) was repeated for a total of 25 rounds. The mineralization polypeptide was SYENSHSQAINVDRT (shADP5; SEQ ID NO:16). Results of the experiment showed that whiteness of the tooth enamel improved with each round of remineralization.

Example 8. Solution Mineralization Approach

Human teeth, donated by the University of Washington School of Dentistry (Seattle, Wash., USA), were selected for their clean, smooth surfaces. The teeth were sterilized in bleach, cut on a diamond blade to remove the root, and halved. A thin layer of the enamel surface was then cut on one of the halves parallel to the previous cut, such that the dentin layer could be seen without completely removing the enamel on the tooth. This allowed imaging of the enamel surfaces after the mineralization experiment without the problem of surface reflection encountered in previous experiments, in addition to a more parallel surface from which to compare the brightness or whiteness results. The cut enamel side of the tooth sample was then sonicated in DI water and polished on diamond slurry smooth out the surface for imaging. The sample was then cut into quarters, with the lower half selected for a tetracycline experiment because of the even distribution of dentin coloring in the lower quarters of the tooth sample. The samples were then stained in 10 mg/mL tetracycline solution for five days.

During mineralization, using a 96-well plate, one of the stained halves was stored in 1200 µL Tris (24 mM) as a negative control, and the experimental sample was incubated in 150 µL shADP5 (0.8 mM) at 37° C. for 10 minutes. The experimental sample was then rinsed of excess peptide with deionized water and then stored in 600 µL $CaCl_2$ (9.6 mM), to which 600 µL monobasic $KH_2PO_4$ (5.76 mM) was added. The well plate containing both the control and experimental samples was then stored at 37° C. for about 24 hours for mineralization to occur on the treated stained tooth sample.

Figure 5:
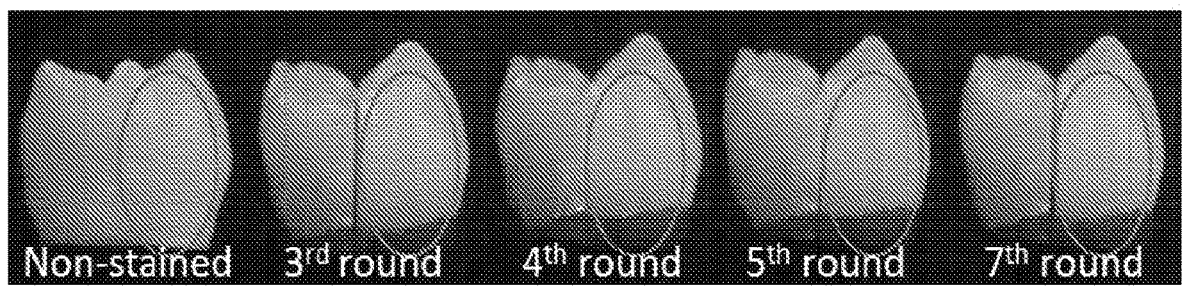
FIG. 5 depicts a tooth before staining, a side-by-side comparison of a stained tooth portion with a 3-rounds remineralized tooth portion, a side-by-side comparison of a stained tooth portion with a 4-rounds remineralized tooth portion, a side-by-side comparison of a stained tooth portion with a 5-rounds remineralized tooth portion, and a side-by-side comparison of a stained tooth portion with a 7-rounds remineralized tooth portion, as described in Example 8.
Figure 6:
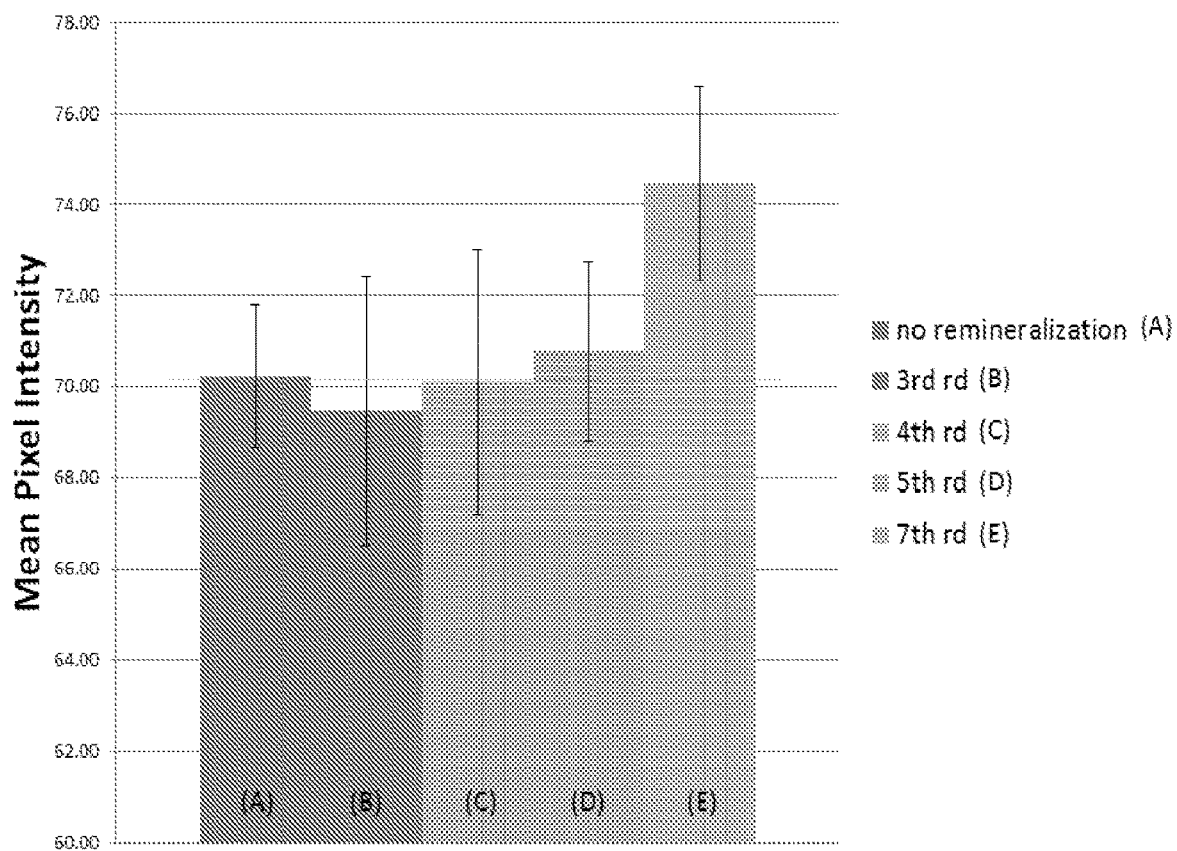
FIG. 6 shows a line profile analysis of the tooth before staining (Bar A), the 3-rounds remineralized tooth (Bar B), the 4-rounds remineralized tooth (Bar C), the 5-rounds remineralized tooth (Bar D), and the 7-rounds remineralized tooth (Bar E), as described in Example 8.
Figure 7:
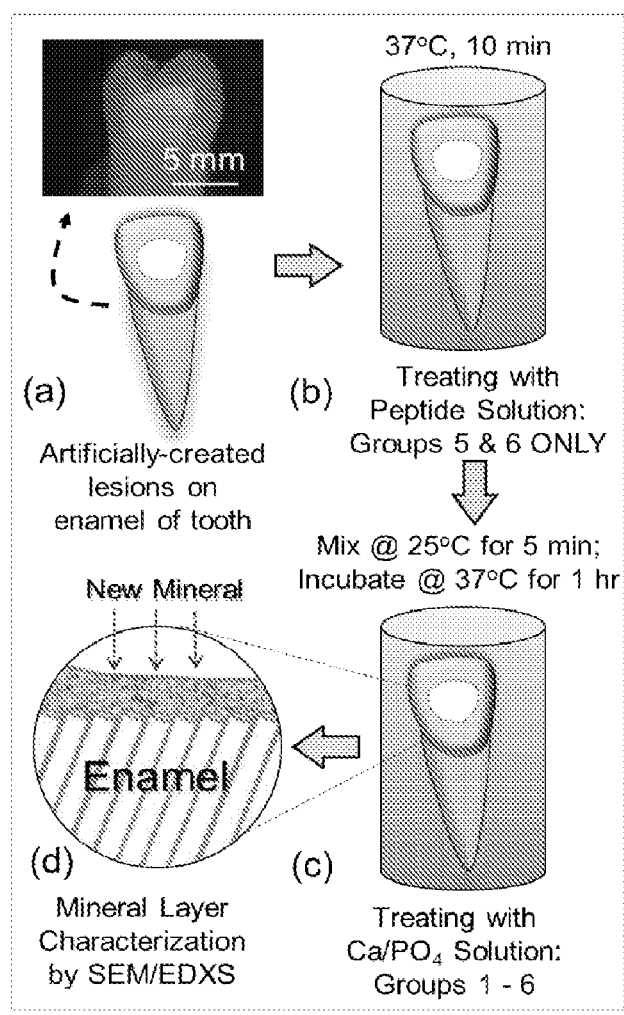
FIG. 7. (a) White spot lesion was artificially created by exposing a window on tooth surface for demineralization; (b) Groups 5 & 6 samples were exposed to shADP5 solution for 10 minutes at 37° C.; (c) Samples were then incubated in $F/Ca^{2+}/PO_4^{3-}$ or $Ca^{2+}/PO_4^{3-}$ solutions for 1 hour at 37° C.; (d) New mineral layer was characterized by SEM/EDXS.

The remineralization process (incubation in polypeptide solution, incubation in solution of ion sources, and rinsing with deionized water) was repeated on the experimental sample for a total of 27 rounds. After 27 rounds of mineralization on the experimental sample, the tooth was inspected for changes in brightness qualitatively. The stained negative control was polished to expose the original enamel stain in order to compare the whitening effect of the peptide mineralization. FIG. 5 shows pictures of the tooth before staining, a side-by-side comparison of the stained negative control sample with the experimental sample having three rounds of remineralization, a side-by-side comparison of the stained negative control sample with the experimental sample having four rounds of remineralization, a side-by-side comparison of the stained negative control sample with the experimental sample having five rounds of remineralization, and a side-by-side comparison of the stained negative control sample with the experimental sample having seven rounds of remineralization. FIG. 6 shows a line profile analysis of the tooth before staining (Bar A), the 3-rounds remineralized tooth (Bar B), the 4-rounds remineralized tooth (Bar C), the 5-rounds remineralized tooth (Bar D), and the 7-rounds remineralized tooth (Bar E). The bar chart in FIG. 6 shows the Mean Pixel Intensity (MPI) of the tooth at the various stages.

The results are as follows, showing effective whitening from use of the biomineralization peptide:

TABLE 4

| Assay | Mean Pixel Intensity | Bar in FIG. 6 |
|---|---|---|
| No staining or remineralization | 70.22 ± 1.57 | A |

TABLE 4-continued

| Assay | Mean Pixel Intensity | Bar in FIG. 6 |
|---|---|---|
| After 3 rounds | 69.47 ± 2.96 | B |
| After 4 rounds | 70.11 ± 2.92 | C |
| After 5 rounds | 70.79 ± 1.96 | D |
| After 7 rounds | 74.47 ± 2.13 | E |

As can be observed from bars (B) to (E) in FIG. 6 and the mean pixel intensity values in the table above, whiteness of the stained tooth improves with repeated rounds of remineralization.

Example 9. Biomimetic Tooth Repair: Amelogenin-Derived Peptide Permit In Vitro Remineralization of Human Enamel White spot lesions (WSL) and incipient caries on enamel surfaces are the earliest clinical outcomes for demineralization and caries. If left untreated, the caries can progress and may cause complex restorative procedures or even tooth extraction which destroys soft and hard tissue architecture as a consequence of connective tissue and bone loss. Current clinical practices are insufficient in treating dental caries. A long-standing practical challenge associated with demineralization related to dental diseases is incorporating a functional mineral microlayer which is fully integrated into the molecular structure of the tooth in repairing damaged enamel. This study demonstrated that small peptide domains derived from native protein amelogenin can be utilized to construct mineral layer on damaged human enamel in vitro. Six groups were prepared to carry out remineralization on artificially created lesions on enamel: (1) No treatment, (2) $Ca^{2+}$ and $PO_4^{3-}$ only, (3) 1100 ppm fluoride (F), (4) 20,000 ppm F, (5) 1100 ppm F and peptide, and (6) Peptide alone. While the 1100 ppm F sample (indicative of common F content of toothpaste for homecare) did not deliver F to the thinly deposited mineral layer high F test sample (indicative of clinical varnish treatment) formed mainly $CaF_2$ nanoparticles on the surface. Fluoride, however, was deposited in the presence of the peptide which also formed a thin mineral layer, which was partially crystallized as fluorapatite. Among the test groups, only the peptide-alone sample resulted in remineralization of fairly thick (10 μm) dense mineralized layer containing plate-like HAp resembling the structure of the healthy enamel. The newly formed mineralized layer showed integration with the underlying enamel as evident by cross-sectional SEM imaging. The approach has potential utility in future clinical implementation as a new, biomimetic remineralization treatment in dental health care.

Dental caries is one of the major public health problems and it is a highly prevalent disease among the global population. Incipient caries and white spot lesions (WSL) as well as hypersensitivity, are the earliest clinical evidence of enamel demineralization and dental caries. Dental caries occurs when tooth enamel is exposed to acid produced by cariogenic bacteria. As a result, acid diffuses into surface enamel and dissolves hydroxyapatite (HAp) mineral. Due to its non-regenerative nature, enamel is unable to heal and repair itself post-demineralization.

Traditionally, fluoride (F) has been used as the key agent in prevention of caries. Fluoride functions primarily via topical mechanisms. It is believed that fluoride forms a thin layer of new but harder mineral, namely fluorapatite (FAp) which is incorporated into the existing HAp mineral on the tooth surface. There is a trend of enhancing the remineralization effect of fluoride with calcium and phosphate supplementation in high risk individuals. Although controversial, the use of fluoride products remains the primary treatment modality for caries prevention and remineralization, with major limitations regarding the efficacy of these products for the reversal or prevention of dental caries. Fluoride delivery systems, therefore, are not sufficient to overcome the high caries risk especially in younger and elderly population.

Although dental caries is a preventable infectious disease, oral health promotion and prevention can fail due to many factors. The advanced cavitation of the carious lesion necessitates restoring the tooth with materials such as metals, composite resins and ceramics to replace the lost enamel or, even, dentin. However modern dental materials to repair cavitated carious lesions are not compatible with biological tissues at the lesion/restorative material interface mainly because of their physical (crystallography and morphology) and chemical differences (elemental compositions and phases) compared to the natural tooth structure. Although treatment of early caries lesions by the application of various types of nano-sized HAp or $CaCO_3$ with or without F has received considerable attention, their clinical validation is still lacking. Low solubility of the calcium phosphates, particularly in the presence of fluoride ions is the main difficulty with the clinical application of remineralization. No clinical remineralization system has emerged to promote biomimetic enamel subsurface remineralization in vivo.

Incorporating a functional and biomimetic mineral layer to the molecular structure of the tooth to repair damaged enamel tissue has been a long standing challenge. A better understanding of peptide-guided remineralization on human tooth and, therefore, the ability to control the mineral layer properties, with no, low or high-F content, has enormous clinical implications to restore enamel and other dental hard tissues. As a major step towards this overarching goal, the objective of this study has been to develop an in vitro, cell-free, natural remineralization model on artificially induced enamel lesions Because of these unique biomineralization characteristic and its short and simple sequence, ADP5 has been used in this research as the active ingredient in solution for the formation of mineralized layer for the purpose of repairing artificially formed defects on the surface of enamel. The work presented herein could eventually form the foundation of developing clinical treatments for the restoration of early stage cavities, e.g., incipient caries, white spot lesions and hypersensitivity.

Materials and Methods

Design of Amelogenin-Derived Peptides, ADPs

The ADP5 peptide was generated using a procedure that was developed for designing protein derived peptides as described previously. Briefly, 7-AA and 12-AA long hydroxyapatite binding peptides (HABPs) were experimentally selected using the c7c- and 12-phage libraries (New England BioLabs Inc., Ipswich, Mass., USA), respectively. Next, the 180 amino acid-long human amelogenin protein (rM180) was divided into 7-AA and 12-AA long segments and each segment was compared with all of the 155 experimentally selected HABPs. The regions with high similarity scores from 7-AA and 12-AA long segments were overlapped and those coinciding high similarity regions were chosen as the putative strong binding regions. These computationally determined high similarity regions were then refined to design the ADPs by protein structure prediction, $Ca^{2+}$ ion-binding domain predictions, and meta-functional signature analyses. Two separate assays were developed to characterize the ADPs: Solid binding affinity to HAp and mineralization in aqueous solution. The prediction in the binding assay was 100% while the biomineralization assay resulted in some surprises. Relevant to this study, although ADP5 is one of the weakest binding peptides, it has the fastest mineralization kinetics, very close to that of full-length amelogenin. Because of this property, ADP5 has been used for developing mineralization on human teeth. One more aspect of ADP5 is that its full length, 25 AA, is difficult to solubilize in water. For this, we eliminated the six amino acids from the amino end and alanine from the carboxyl end, while keeping the charged amino acids intact that are thought to initiate mineralization. The originally designed ADP5 was generated from mouse amelogenin; for shADP5 K in the sequence was replaced by N, where "s" stands for "short" and "h" for "human". The shADP5 peptide was synthesized by solid phase peptide synthesis CSBio 336s (CSBio, Menlo Park, Calif., USA) automated peptide synthesizer and purified by reverse phase high performance liquid chromatography. The masses of the purified peptide and its purity were confirmed by using MALDI-TOF mass spectrometer (Bruker Daltonics, Billerica, Mass., USA). Molecular characteristics of the shADP5 peptide used in this work are listed in Table 8.

Sample Preparation and Test Groups:

Extracted teeth with no visible white spot lesions, caries, or any other kind of restorations were collected from dental clinics around the King County area (WA, USA) and disinfected in 10% aqueous bleach solutions. Prior to the experiments, the teeth were cleaned to remove visible blood, gross debris and soft connective tissue using a dental scaler under a light microscope.

Formation of Artificial Lesions

Enamel was demineralized to create artificial lesions to mimic white spot lesions and/or incipient caries. The teeth were covered by lacquer leaving a 4-mm wide square window in the enamel close to cemento-enamel junction. The exposed areas of 4×4 mm enamel were treated with a cocktail of acetic acid/$CaCl_2$/$KH_2PO_4$ for 2 weeks to establish up to 200 μm deep artificially created non-cavitated white spot lesions (WSL). Samples were then divided into control and test groups. Test groups were treated either with peptide, fluoride, or combination of both (Table 5).

TABLE 5

Experimental Test Groups and Mineralization Treatments.

| Test Groups | Treatment | # of samples |
|---|---|---|
| Group-1: (Negative control) | No Treatment | 5 |
| Group-2: ($Ca^{2+}$ and $PO_4^{3-}$ Only) | 4.8 mM $Ca^{2+}$/2.88 mM $PO_4^{3-}$, 1 hour | 5 |
| Group-3: (Low concentration F) | 1100 ppm F (common fluoridated toothpaste concentrations), 4.8 mM $Ca^{2+}$/2.88, mM $PO_4^{3-}$ | 5 |
| Group-4: (High concentration F) | 20,000 ppm F (dental varnish concentration), 4.8 mM $Ca^{2+}$/2.88 mM $PO_4^{3-}$, 1 hour | 5 |
| Group-5: (shADP5 with low concentration F) | 1. 0.8 mM Peptide, 10 minutes 2. 1100 ppm F + 4.8 mM $Ca^{2+}$/2.88 mM $PO_4^{3-}$, 1 hour | 5 |
| Group-6: (shADP5) | 1. 0.8 mM Peptide, 10 minutes 2. 4.8 mM $Ca^{2+}$/2.88 mM $PO_4^{3-}$, 1 hour | 5 |

Peptide Design and Synthesis

The peptide shADP5, shortened ADP5, was generated using a procedure that was developed for designing protein-derived peptides, as described previously[31] (see also short synopsis of the procedure in Supporting Information). The peptide (Table 6) was synthesized by using an automated solid-phase synthesizer (CS336X; CS-Bio, Menlo Park, Calif., USA) through Fmoc-chemistry. In this procedure, in the reaction vessel, the Wang resin (Novabiochem, West Chester, Pa., USA), was treated with 20% piperidine in DMF to remove the preloaded Fmoc group. Next, the incoming side chain protected amino acid was activated with HBTU (Sigma-Aldrich, St Louis, Mo., USA) in dimethylformamide (DMF, Sigma-Aldrich, St Louis, Mo., USA) and then transferred into the vessel where it was incubated with the resin for 45 min. After washing the resin with DMF, this protocol was applied for the addition of each of the next amino acids and synthesis reaction was monitored by UV-absorbance at 301 nm. Following synthesis, the resulting resin-bound peptides were cleaved and the side-chain de-protected using reagent-K [TFA/thioanisole/$H_2O$/phenol/ethanedithiol (87.5:5:5:2.5), Sigma-Aldrich, St Louis, Mo., USA] and precipitated by cold ether. Crude peptides were purified by RP-HPLC with up to >98% purity (Gemini 10u C18 110A column). The sequence of the peptides was confirmed by a MALDI-TOF mass spectrometry with reflectron (RETOF-MS) on an Autoflex II (Bruker Daltonics, Billerica, Mass., USA).

TABLE 6

Molecular characteristics of the peptide shADP5.

| Peptide | Sequence | MW | pI | G.R.A.V.Y. | Net Charge |
|---|---|---|---|---|---|
| shADP | S*Y*ENS*H*SQAIN*V*DR*T** (SEQ ID NO: 16) | 1720.7 | 5.30 | -1.273 | -1 |

*Bold font AAs are polar, uncharged residues; underlined residues are hydrophobic; italicized residues are charged residues
G.R.A.V.Y. is grand average of hydropathy (see web site gravy-calculator.de/)

Re-Mineralization Protocol

Prior to remineralization, samples requiring peptide treatments (Groups 5 & 6) were incubated in 50 μL of 0.8 mM peptide dissolved in 50 mM Tris Buffer Solution (TBS) (pH:7.4) for 10 minutes at 37° C. Next, treatment samples were exposed to 50 mM TBS containing $Ca^{2+}$/$PO_4^{3-}$ (Groups 2, 5) or $Ca^{2+}$/$PO_4^{3-}$/$F^-$ (Groups 3, 4, 6) at concentrations as listed in Table 5 for 1 hour at 37° C., then rinsed with de-ionized (DI) water, dried by forced air and stored at room temperature until characterization.

Sample Characterization by SEM and EDXS Analyses—Imaging and Elemental Composition:

After re-mineralization experiments were completed, secondary electron imaging (SEI) in the scanning electron microscope (SEM) was used to characterize the surface morphology and to show the thickness of newly formed mineral layer in cross-sections where applicable. Specimen preparation for SEM involved cutting a notch on the back side using a low speed saw (IsoMet™, Buehler, Lake Bluff, Ill., USA) before they were subjected to WSL formation and remineralization as described above. After remineralization step was completed, specimens were rinsed with DI water, air dried gently (<5 PSI), then carefully fractured into 2 pieces along the notch. One of the fractured pieces was mounted on a SEM stub with the mineralizing surface facing up for imaging the surface morphology and second piece was mounted with the cross-section facing up to show the thickness of mineral layer. Mounted specimens were then stored in vacuum for at least 2 hours to remove residual moisture which were then sputter coated with 5-nm thick platinum (SPI-Sputter Module Coater, SPI Supplies, West Chester, Pa., USA). SEM characterization was performed using an FEI Sirion microscope (Sirion, FEI, Hillboro, Oreg., USA) operating at 10 kV acceleration voltage. The chemical composition was measured by an onboard energy dispersive X-ray spectroscopy (EDXS) system (X-Max$^N$ Si drift detector with AZtecEnergy software package, Oxford Instruments, Abingdon, Oxfordshire, UK). The measurements for each group were pooled from 5 specimens per group. The average values and standard deviations were calculated and expressed as the mean±standard error.

Structural Characterization by Transmission Microscopy (TEM)

After remineralization steps were completed, TEM samples were collected by carefully shaving off the top most surface of the remineralized layer from the artificially created white spot lesion using a clean razor blade. The shaved particles were suspended in 100% ethanol, and the suspension was drop-casted onto a carbon coated TEM grid, which was then vacuum dried before TEM characterization. TEM bright field imaging (BF) imaging and selected areas diffraction were carried out using an FEI Tecnai (FEI, Hillboro, Oreg., USA) operating at 200 keV.

Mechanical Properties Characterization

Similar to SEM specimen preparation, tooth samples were notched from the back of tooth before remineralization, then fractured along the notch. The specimens were then mounted in a room temperature-cure epoxy, and the cross-section of the fracture was polished to 0.1 µm finish using diamond lapping films (Allied High Tech Products Inc., Rancho Dominguez, Calif., USA). Nanoindentation measurements were made using a Triboindentor nanoindentation system (Hysitron Inc., Minneapolis, Minn., USA) in air. Hardness (H) and elastic modulus ($E_r$) were determined by the software accompanying the nanoindentation unit.[40-42] In order to obtain the values that were not indentation volume dependent, maximum indentation depth for all measurements kept at 120±10 nm. All reported H and $E_r$ values were averaged over 20 measurements.

In addition to nanoindenation measurements, microhardness was also performed on the surface to quantitatively assess the mechanical properties of the mineral layers with larger areas and volumes including the underlying enamel as a composite. Vicker's microhardness was performed on at room temperature using Vicker's indenter on a Wilson Hardness Tukon 1202 microhardness tester at 10 kg applied load (Illinois Tool Works, Lake Bluff, Ill.). At least 20 measurements per group were recorded for obtaining an average and statistical analysis.

Results

Figure 8:
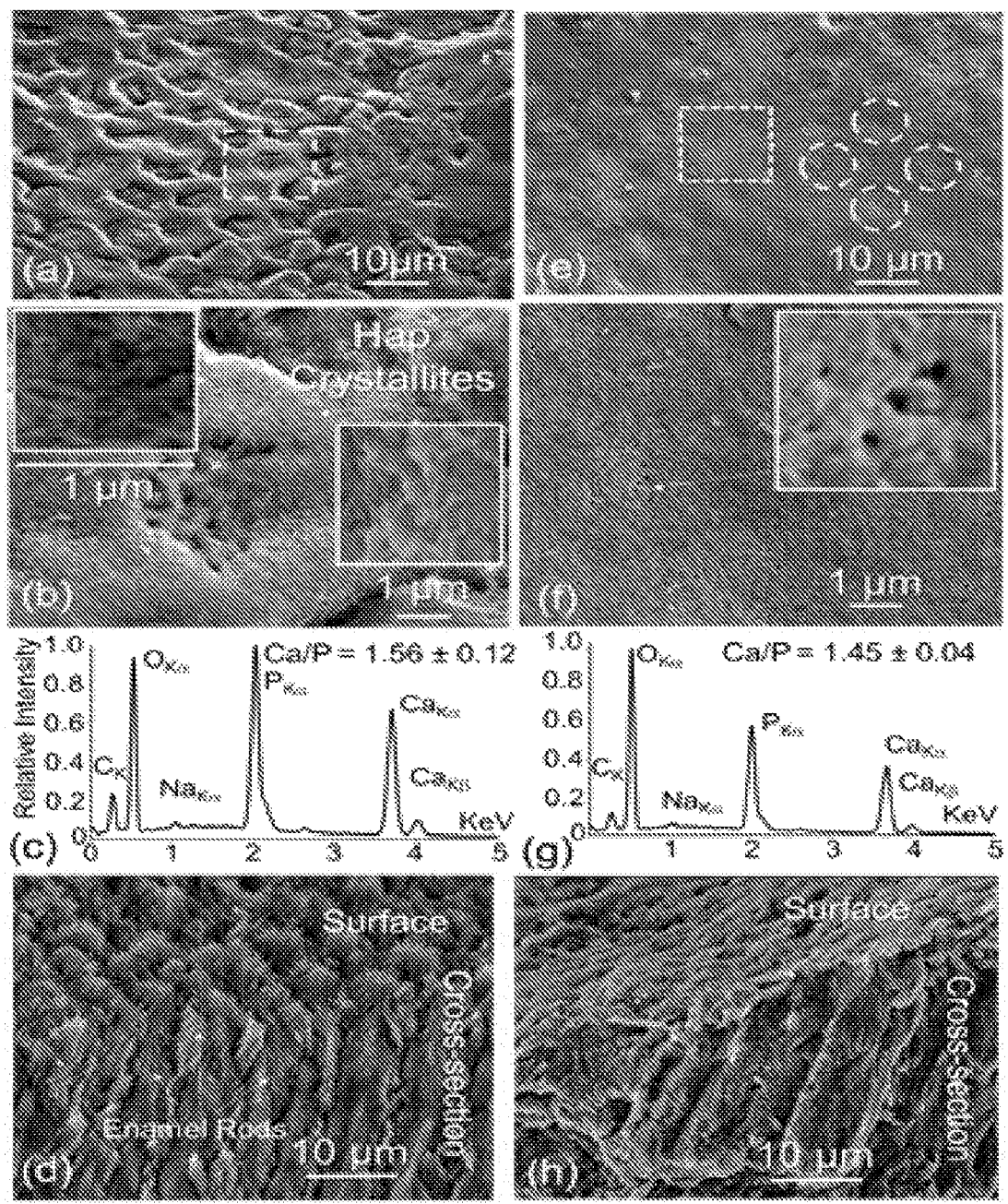
FIG. 8. Face-on (a,b) and edge-on (d) SEM images and EDXS analyses (c) of Group 1: Negative Control. Face-on (e,f) and edge-on (h) SE images and EDXS analysis (g) of Group 2: $Ca^{2+}$ and $PO_4^{3-}$ only. Insets in 2b and 2f show enamel rods and HAp plate-like crystallites exposed on the surface of damaged enamel as a result of demineralization. The inset panels are 1 μm×1 μm.

The incubation of samples in demineralization cocktail exposed enamel rods on the surface of the samples before the re-mineralization treatment was undertaken, as shown in Group 1-Negative Control (FIG. 8a-b). Elemental chemical analysis of the surface by EDXS gives a ratio of $Ca^{2+}/PO_4^{3-}$ 1.56±0.12 (FIG. 8c). As seen in the cross-sectional view of (FIG. 8d), well aligned enamel rods of ~3 µm diameter extend to the exposed surface where they display HAp crystallites constituting the rods. After 1-hour of exposure to $Ca^{2+}/PO_4^{3-}$ solution, no substantial re-mineralization was observed on the samples in Group 2. Considering that the imprints of enamel rod remained visible as shallow depressions on the enamel surface (FIG. 8e-f) any possible deposit of solid material, possibly the result of $Ca^{2+}$ and $PO_4^{3-}$ ions reacting to form an amorphous deposit, remained extremely thin. In fact a very thin (<1 µm) layer is barely visible in the SEM image of the cross-sectioned sample shown in FIG. 8h. Elemental analysis of the surface by EDXS gives a ratio of $Ca^{2+}/PO_4^{3-}$ 1.45, possibly indicating a mixed mineral composition (FIG. 8g; also see Table 7).

TABLE 7

Elemental composition analyses of the remineralization test groups by EDXS.

| Test Group | Remineralized Layer | | | Possible Mineral Formed |
|---|---|---|---|---|
| | Ca/P | Ca/F | Ca/O | |
| 1. Control | 1.56 ± 0.12 | — | 0.51 ± 0.11 | Only HAP |
| 2. Ions only | 1.45 ± 0.04 | — | 0.28 ± 0.02 | Amorphous Ca—P transition phase |
| 3. Low F | 1.69 ± 0.05 | 36.99 ± 2.9 | 0.74 ± 0.15 | Ca—P—F transition phase + $CaF_2$ |
| 4. High F | 5.62 ± 0.96 | 0.49 ± 0.11 | 1.01 ± 0.16 | Mainly $CaF_2$ |
| 5. Low F + Peptide | 1.60 ± 0.11 | 8.74 ± 0.78 | 0.34 ± 0.18 | FAP ± some $CaF_2$ |
| 6. Peptide only | 1.56 ± 0.12 | — | 0.56 ± 0.13 | Only HAP |

Figure 9:
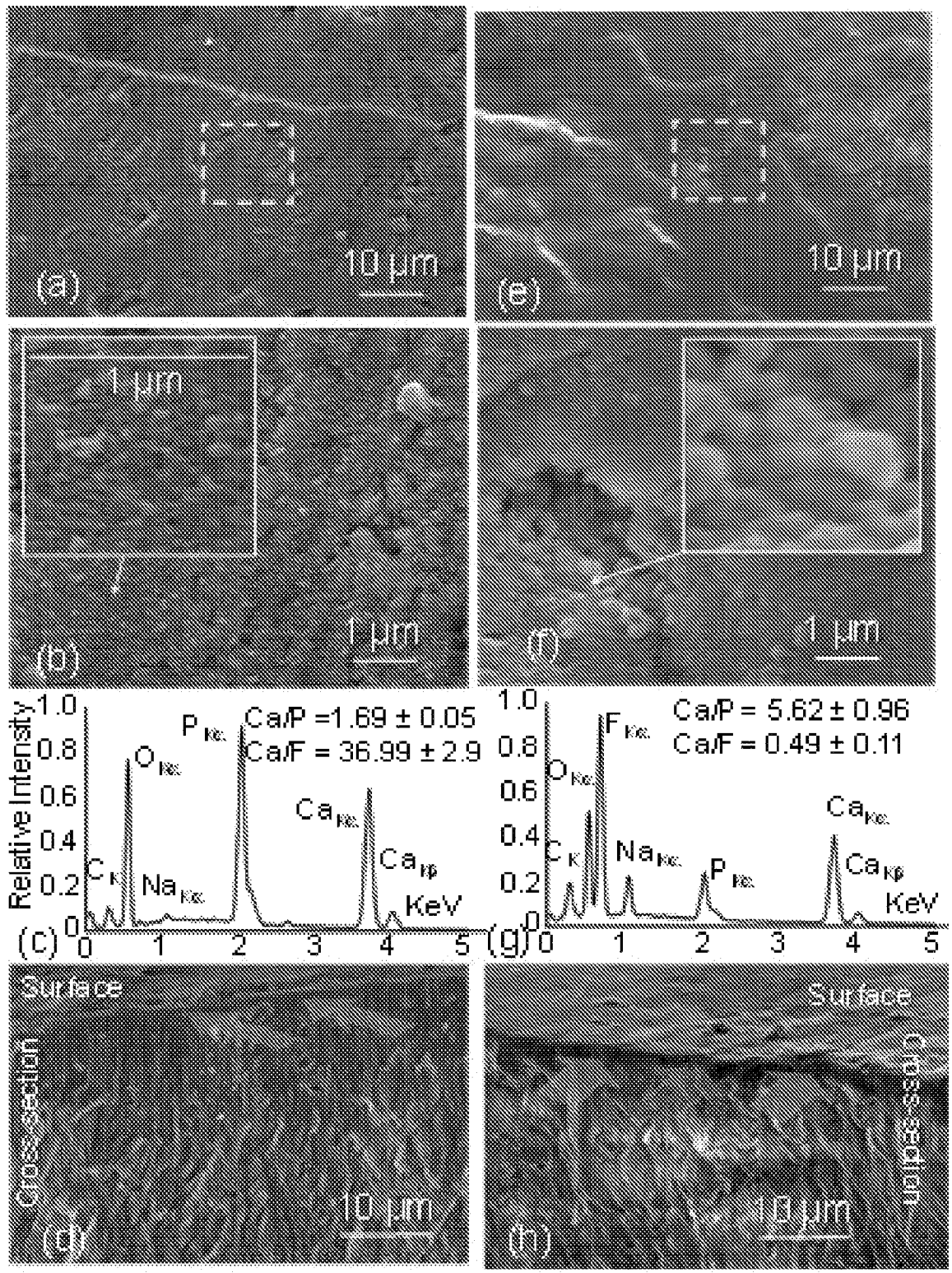
FIG. 9. Face-on (a,b) and edge-on (d) SEM images and EDXS analysis (c) of Group 3: 1100 ppm $F+Ca2+/PO_4^{3-}$. Face-on (e,f) and edge-on (h) SEM images and EDXS analysis (g) of Group 4: 20,000 ppm $F+Ca2+/PO_4^{3-}$. Insets in 3b and 3f show loosely packed nanospherical particles (of dia. ~20-30 nm) as a result of F deposition. The inset panels are 1 μm×1 μm.

In Group 3 (low concentration fluoride), 1100 ppm F was applied in the presence of $Ca^{2+}$ and $PO_4^{3-}$ ions. The concentration of 1100 ppm fluoride corresponds to the concentration of the most commonly used toothpaste available over the counter for daily home care.[5-7] The analysis of the SEM images recorded from the surface suggests non-uniformly deposited layer with a fine (<1 µm) roughness compared to the surface formed without the fluoride in Group 3 (FIGS. 9a-b). A detailed analysis of the surface structure, e.g., at higher magnification image in FIG. 9b, reveals fine nanoparticles of diameter 20-50 nm. The cross-sectioned samples reveal a new layer with a thickness of about 1 µm covering the surface of enamel in the lesion (FIG. 9d). The elemental composition analysis from the surface revealed prominent peaks of $O_{K\alpha}$, $P_{K\alpha}$, and $Ca_{L\alpha}$ as well as a small peak corresponding to $F_{K\alpha}$. Ca/F ratio gives a values of more than 30 while the Ca/P ratio is close to 1.70 (FIG. 9c).

In Group 4 (high concentration fluoride), 20,000 ppm fluoride (concentrations of most commonly used dental varnishes) applied with $Ca^{2+}$ and $PO_4^{3-}$ ions. The analysis of the SEM images recorded from this treatment displayed significantly different surface topography, structures, and elemental composition as compared to the samples in the previous groups of non-fluoride or low concentration F treatment. Although at low magnifications (FIG. 9e) the surface appears fairly smooth, higher magnification (FIG.

9f) revealed small spherical particles of 100-200 nm diameter covering the overall surface (indicated by arrow in FIG. 9f). The SEM secondary electron images recorded from the cross-sectioned samples reveal an about a micrometer-thick new layer on the surface of the teeth (FIG. 9h). The EDXS spectra received from the surface gives a high concentration of $F_{K\alpha}$ peak, the most prominent among all the peaks in the spectra from this group of samples (FIG. 9g). The quantitative analysis of the spectra from the samples prepared in this group exhibited the C/F ratio of 0.49 (Table 7).

Figure 10:
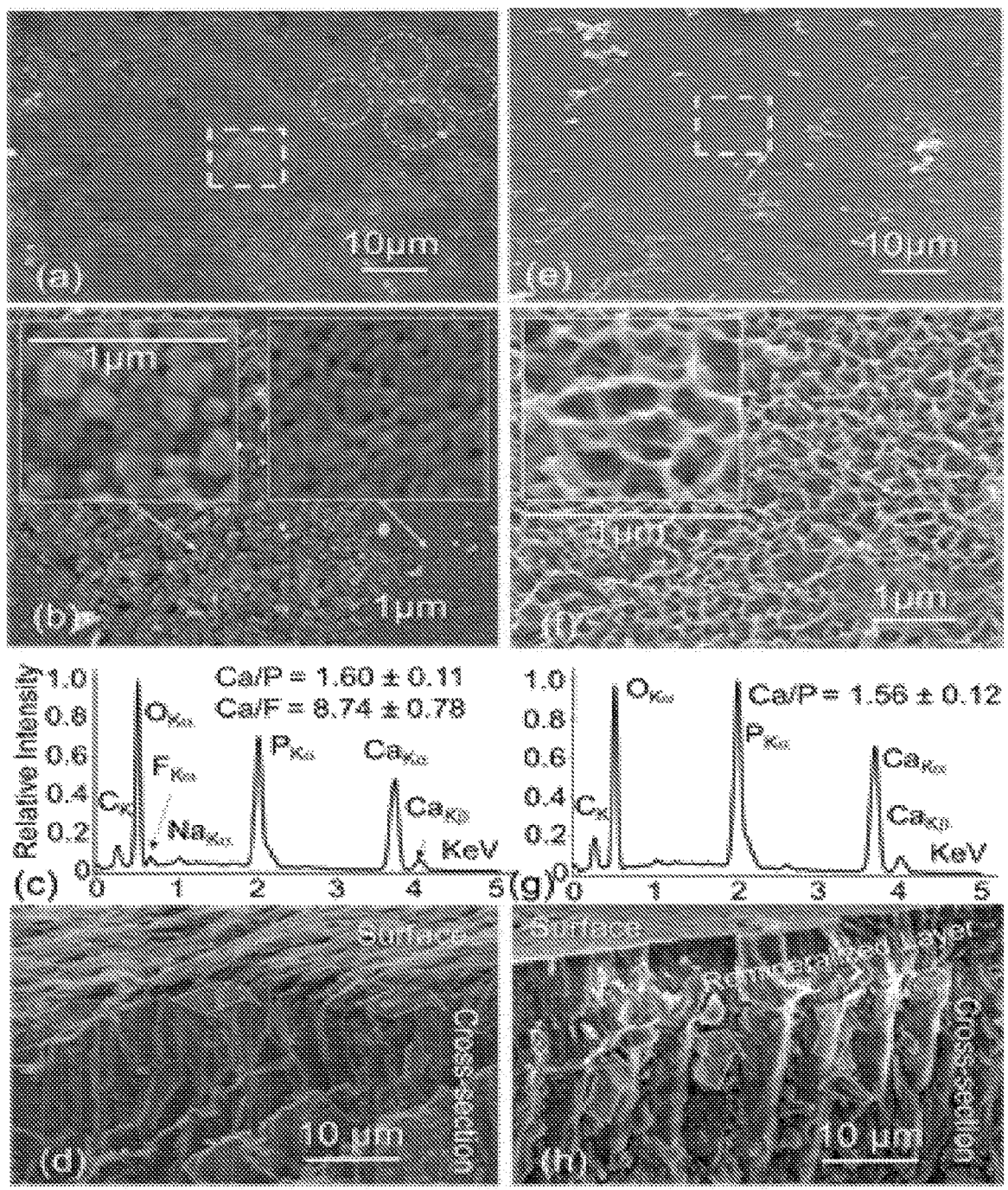
FIG. 10. Face-on (a,b) and edge-on (d) SEM images and EDXS analyses (c) of Group 5: shADP5+1100 ppm $F+Ca^{2+}/PO_4^{3-}$. Insets in 4b show loosely crystallized regions of accumulated 100-nm dia. spherical nanoparticles on the surface. Face-on (e,f) and edge-on (h) SEM images and EDXS analysis (g) of Group 6: shADP5+$Ca^{2+}/PO_4^{3-}$. Inset 4f displays a highly uniform, plate-like HAp crystallites within newly formed (h) mineral layer in shADP5+$Ca^{2+}/PO_4^{3-}$ treatment. The inset panels are 1 μm×1 μm.

In group 5 (the peptide with low concentration fluoride) shADP5 was applied with 1100 ppm fluoride along with $Ca^{2+}$ and $PO_4^{3-}$. The surface microstructure of the samples carried out by SEM showed fairly smooth surface with about 1-2 μm thickness (FIG. 10a-d). Enamel rod imprints remained visible in the lower magnification image (FIG. 10a). Higher magnification image of the sample surface, however, exhibits two different surface morphologies (see insets in FIG. 10b); somewhat loosely deposited nanoparticles of 50-100 nm diameter and dense structure composed of rod-like nanoparticles of few tens of nanometers in diameters with the diameter/length aspect ratio of 1/5. Elemental analysis of the samples from this group revealed fairly noticeable $F_{K\alpha}$ peak in addition to highly prominent $Ca_{K\alpha}$ and $P_{K\alpha}$ peaks with the elemental ratio of Ca/F, 8.7 (FIG. 10c).

In the Group 6 (shADP5+$Ca^{2+}$/$PO_4^{3-}$), the SEM images in FIG. 10e-f give a continuous layer of plate-like crystals growing from the surface of the underlying enamel lesion when the surface is exposed to aqueous peptide plus $Ca^{2+}$/$PO_4^{3-}$ Compared to the negative control (Group-1) or low concentration fluoride treatment (Group-3), the enamel rod imprints in the face-on images are no longer visible, indicating that the new mineral layer is thick enough to mask the exposed enamel rods (FIG. 10e-f). The cross-section image in FIG. 10h shows a 10 μm thick continuous remineralized layer with fairly smooth surface topography. Elemental analysis of the samples from this group revealed prominent $Ca_{K\alpha}$, and $P_{K\alpha}$ peaks with a ratio of 1.54±0.12; this is close to ideal ionic ratio of 1.6 in HAp composition (FIG. 10g; Table 7).

Figure 11:
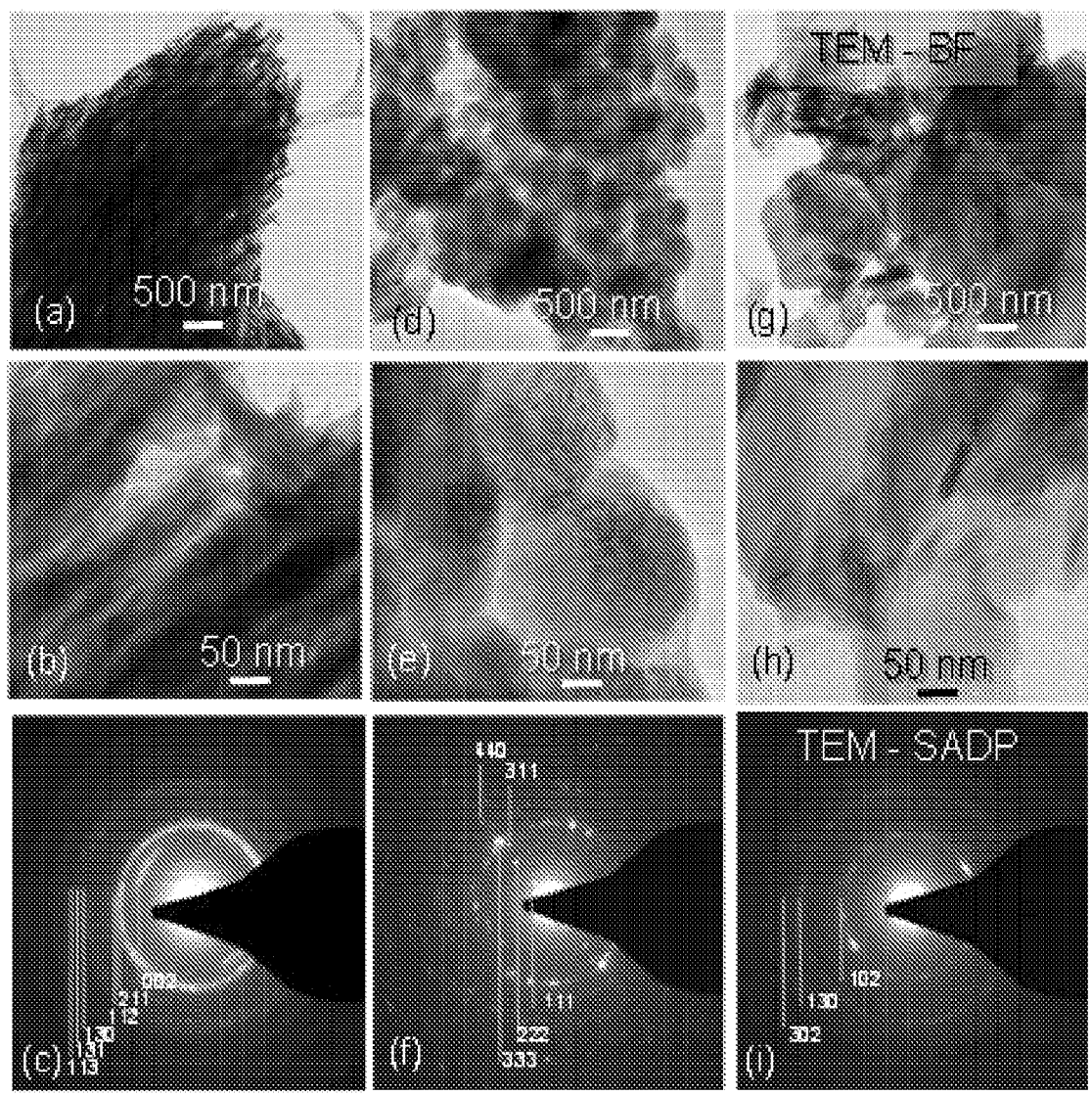
FIG. 11. TEM bright field images and corresponding selected diffraction for no treatment negative control (group 1) (a-c), high concentration F treatment (group 4) (d-f), and peptide treatment (group 6) (g-i).

To further analyze the structural characteristics of the mineral layers in experimental group, imaging and diffraction analyses were carried out on samples by using transmission electron microscopy. The TEM samples were prepared by gently shaving fragments off the surface of tooth specimens. Group 1, which received no remineralization treatment, enamel fragments were analyzed. As shown in FIG. 11 a-c, textured elongated HAp crystals of 30-50 nm were encountered, typical of those in enamel rods in healthy enamel tissue. In the case of high concentration F treatment (group 4), generally round particles $CaF_2$ in the range of 100-250 nm in diameters were observed (FIG. 11 d-f). On the peptide treatment group (group 6), large particles (in the shown projection) of HAp were found (FIG. 11 g-i) possibly corresponding to plate-shape mineral particles. It is noted that groups 2, 3 and 5, had structural characteristics similar to those of group 1 were discovered (data no shown here but displayed in the SI section). It should be noted, however, that in all cases, it was challenging, but not impossible (as demonstrated in FIG. 11 above) to differentiate the newly formed crystallites from those HAp crystallites in the underlying enamel.

Mechanical properties of the mineralized layers were determined from two tests. First, the microhardness test was carried out using a Vicker's indenter loading on the mineralized tooth surface. The hardness for the negative control group (Group 1), i.e. no treatment was 130.1±10.4 HV10. This was the baseline figure representing microhardness of the surface of bare artificially created WSL which other experimental groups compared against. As the reference, the microhardness tests were also conducted on healthy enamel and healthy dentin, away from the mineralized surface, and displayed in Table 8. As shown in Table 8, values for groups 2 to 5 ranged between 129.6±14.9 HV10 to 133.7±12.9 HV10. Student's t-test between group 1 and each of these groups revealed no statistically significant difference (p>0.05). Microhardness of group 6 had slightly higher average value of 140.6+11.3 HV10. Student's t-test against group 1 revealed significant difference with p<0.01. The results indicate that the microhardness values of group 6 as well as the rest of experimental groups fell between that of enamel and dentin.

TABLE 8

Vicker's microhardness of all experimental groups, n ≥ 20.

| Test Groups | Hardness (HV10, MPa) |
| --- | --- |
| Group 1 (Negative Control) | 130.1 +/− 10.4 |
| Group 2 (CaPO₄ Only) | 132.5 +/− 14.9 |
| Group 3 (Low Conc. F) | 129.6 +/− 13.8 |
| Group 4 (High Conc. F) | 131.9 +/− 13.3 |
| Group 5 (shADP5 + Low Conc. F) | 133.7 +/− 12.9 |
| Group 6 (shADP5) | 140.6 +/− 11.3 |
| Healthy Enamel | 290.3 +/− 36.4 |
| Healthy Dentin | 63.3 +/− 3.0 |

Figure 12:
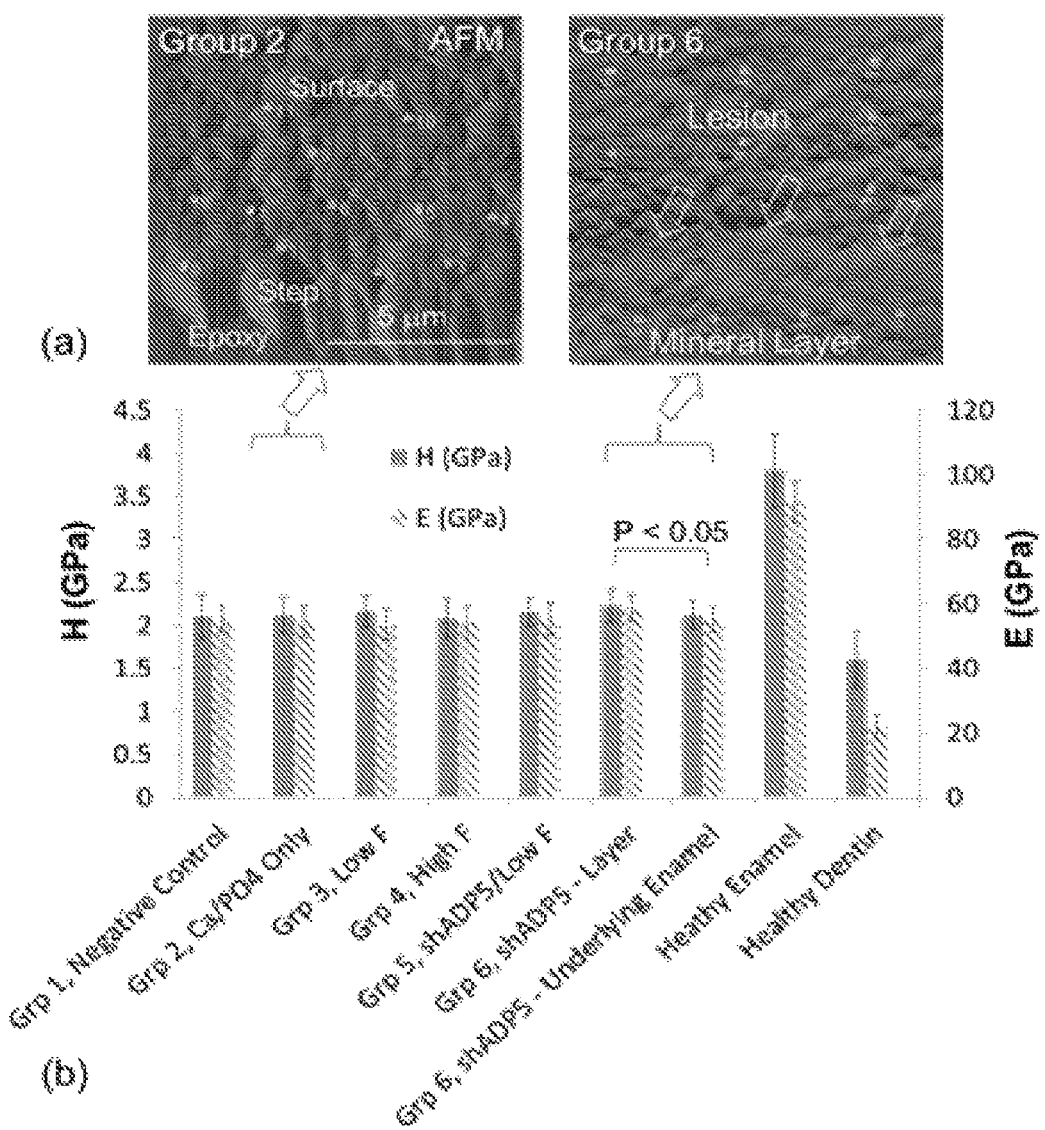
FIG. 12. (a) Atomic force microscope images of the surfaces of the mineralized layers in samples from Group 2 (left) where there is no apparent mineral layer on the lesion and Group 6 (right) showing a clear boundary between the lesion and newly formed mineral layer (arrows). (b) Hardness (left) and elastic modulus (right) of the experimental groups used here as measured by nanoindentation, n>20.

Second mechanical tests were conducted at the nanometer-scale by nanoindentation which not only provides hardness (H) values but also elastic modulus ($E_r$), and the test could be carried out spatially selected regions as the test facilitates scanned surface images. Therefore, nanoindentation tests of all the experimental groups were conducted in cross-sectioned geometry, i.e., indentor direction is parallel to the surface (as opposed to vertical in microhardness tests). The results are tabulated in FIG. 12. Similar to the trend shown in the microhardness data, significant differences were not encountered between group 1 (no treatment negative control) and each of groups 2 through 5 in both hardness and reduced elastic modulus, p>0.05 in all cases. However, observed here again, the average hardness and elastic modulus for group 6 were higher than that of no treatment group 1 with hardness of 2.23±0.23 GPa vs. 2.10±0.36 GPa, p=0.02 and elastic modulus of 58.6±4.7 GPa vs. 55.1±4.3 GPa, p=0.02. Not surprisingly the healthy enamel and dentin had respectively higher and lower values of both hardness and elastic moduli compared to the experimental groups involving remineralization. In conclusion, the mechanical properties (H and E) are higher than those of dentin, but lower than the healthy enamel.

Discussion

A natural, cell-free, biomimetic model was developed to re-mineralize artificially induced lesions on human enamel using a 15-amino acid long amelogenin-derived peptide, shADP5, along with properly tuned ionic concentrations of $Ca^{2+}$/$PO_4^{3-}$ in vitro in the presence and absence of lower and higher fluoride content which were chosen based on the values in the frequently used present dental treatments.

There are drastic differences in the surface characteristics among the 6 groups. First of all, the surface of the artificially demineralized enamel displayed enamel rods, which appeared up to 3-μm diameter depressions exposed on the surface (FIG. 8a-b and FIG. 11a-c). Other prominent feature on the surface was the fine structure of the individual rod-shaped HAp crystallites of a few tens of nm thickness of which make up the enamel rods. However, variations in the microstructure of the artificially demineralized enamel were observed on different tooth samples. As a result of demineralization, the enamel rods of some specimens were more prominent than other samples due to individual differences in tooth structure and cross-section orientation which explains the differences in their apparent local morphology and composition on the surfaces of the teeth samples.

When ionic precursors are used alone (Group 2), this resulted in a thin (<1 µm) layer with a highly porous morphology. The composition was off stoichiometric, i.e., Ca/P ratio of <1.5 which might be due to the formation of calcium-phosphate transition phases (Table 7 and Table 9). We next studied the effect of fluoride on mineral formation which was examined under two different fluoride ion conditions, 1100 ppm in Group 3 and 20,000 ppm in Group 4, which were specifically chosen to mimic the fluoride concentrations of everyday tooth paste and clinical fluoride varnish used in the clinic, respectively. Close examination of the surface structures of the teeth in these two treatments revealed different morphologies. First of all, fluoride treatments resulted in aggregates of nanoparticles in Group 3, and a thin mineralized layer; about 1 µm in Group 4. The layers were composed of nanoparticles which were about an order of magnitude smaller in Group 3 than in Group 4 samples, 20 nm versus 200 nm, respectively. The application of fluoride in dental care products primarily focus on remineralization that is aided by fluoride or incorporation of fluoride into the existing HAp structure, desirably forming fluorapatite (FAp). In this respect, the results of the elemental analyses obtained from the fluoride-treated surfaces are quite intriguing. The Group 3 samples, with low-F, presented hardly any F peaks in the EDXS spectra, giving Ca/F ratio of almost 40. The elemental composition analysis of the sample surface displayed relatively high relative peaks of $O_{K\alpha}$, $P_{K\alpha}$, and $Ca_{L\alpha}$ as well as a small peak corresponding to $F_{K\alpha}$ ($Na_{K\alpha}$ and $Cl_{L\alpha}$ peaks are from the treatment solutions). Possible sources of the low F concentration might be explained either due to the formation of very thin layer of the deposited solid on the surface resulting in the signals originating from the underlying healthy enamel as measured in the majority of EDXS or due to the very low amount of F incorporated into the newly formed surface layer. The lack of sufficient elemental composition of F in the newly formed layer may imply that majority of F was not delivered to the desired mineralization site on the enamel surface in the peptide-free samples. The presence of nanoparticles deposited on the surface forming a thin layer, therefore, may be due to F reacting with excess Na in the buffer solution forming NaF.

In Group 4, the results from face-on and edge-on images illustrated that the new layer is predominantly composed of aggregation of spherical nanoparticles. Considering the ideal Ca/F ratio of 0.5 in $CaF_2$ (Table 9, and FIGS. 11d-f TEM results), the spherical particles might be $CaF_2$ mineral. Another major difference in this group was the value of $Ca_{K\alpha}/P_{K\alpha}$ ratio, which was more than 5.0. Even considering that some of the Ca ions might be confined in $CaF_2$, this ratio still indicates unusually high concentration of Ca trapped in the newly formed layer on the enamel surface. $CaF_2$ is a highly stable compound that could form under the experimental conditions of this study. Instead of the intended apatite compound, the mineral formed in this group was most likely calcium fluoride. Although the ideal ratio of Ca/P is 1.6 for HAp (Table 3), neither of the F-alone samples revealed such concentration ratio. The significance of this result mean that F-alone was not delivered to the tooth surface and, as a consequence, was not incorporated into the enamel or remineralized structure on the surface under the experimental conditions. The question remains therefore that during the clinical and everyday applications of fluoride whether the same formation takes place, i.e., $CaF_2$ materialization instead of incorporation of F into the HAp mineral within the tooth structure.

In the last two groups of test samples (Group 5 and 6) shADP5 peptide was used as part of the precursors during the remineralization experiments. In Group 5, remineralizing peptide shADP5 was applied in the presence of 1100 ppm fluoride. Under low concentration of F, the spherical particles had a tendency to form island aggregates as opposed to being widely disseminated on the demineralized enamel surface compared to the same fluoride concentration without shADP5 in Group 3. Enamel rod imprints remained visible in the lower magnification image (FIG. 10a-b) although these are less prominent than those of no-treatment samples (FIG. 8a-b). The resulting mineralized structure presented two morphologies: the first one was clusters of 50-100 nm diameter spherical nanoparticles accreted non-uniformly on the surface; and the second structure was primarily composed of highly dense nanorods. There was considerably more prominent F peak compared to the no peptide samples, with an overall Ca/F ratio of 8.74±0.78. This explains that there was considerably more F in the mineral formed with the peptide and low fluoride treatment compared to the low fluoride concentration only, (Ca/F=36.99±2.9). If the presence of FAp is considered, i.e., corresponding to the dense nanorods, the ideal ratio of Ca/F is 5.0 (Table 7), then the rest of the fluoride in the mineral layer could be accounted for the formation of NaF nanoparticles. Considering that the observed Ca/P ratio reflects either HAp or FAp stoichiometry (Table 7), the conclusion could be drawn here that the new mineral was formed on the teeth surfaces by partially incorporating F in the presence of peptide. The presence of F could be explained in, at least, two ways; either the fluoride was incorporated into the newly forming HAp mineral replacing OH partially or both HAp and FAp were formed on the surface. In both cases, the effect of peptide appears to be necessary to incorporate fluoride into the structure since in the absence of shADP5, very little or no F was found in the remineralized layer. This may mean that the materials used in the current treatments, e.g., pastes, gels, varnish, and solutions, would contain peptide as a means to effectively mineralize HAp and but also as a carrier for F to the newly mineralized layer and effectively incorporating into it.

In Group-6, in addition to calcium and phosphate precursors, shADP5 peptide was included in the solution. In this case, a thick (>10 µm) remineralized layer formed on the surface composed of plate-like crystal morphology. Considering that this crystal habit is specific to HAp among the calcium phosphate polymorphs and the observed Ca/P ratio is 1.56 which is close the ideal HAp composition, the shADP5 peptide was capable to form a newly mineralized layer composed of HAp crystallites (FIG. 11g-i), demonstrating the remineralizing capability of this peptide as well as layer formation covering the damaged enamel on the human tooth surface. Measuring microhardness of each experimental group on the surface was a way to assess the mechanical properties of the mineralized surface of the experimental groups versus no treatment negative control group in a loading direction relevant to functional dentition loading while using the lowest possible Vicker's indentation load maximize the contribution from the mineralization layer. Even with this lowest load, however, the Vicker's indentor was likely to be penetrating through the thin mineralized layers in groups 2-5; this explains that there are no measurable differences discernable among these groups and the no-treatment negative control group. This explanation is further supported by the SEM observations which showed mineral layers in groups 2 through 5 were in the order of a few μm (perhaps as thin as 1 μm), and with some discontinuity. Because the mineral layer was much thicker in group 6, not only a real difference in microhardness was detected compared to the negative control group, it is revealed that it was significantly harder, though only slightly. The small mineral layer thickness can also explain no detectable difference by nanoindentation in cross-section between group 1 and groups 2-5. It is indeed challenging to discern the mineral layer and underlying WSL in groups 2 to 5 when performing the measurements. The higher Vicker's hardness in the peptide mineralization group (group 6) compared well to the control group (group 1). Combined with the higher hardness in cross-section orientation, measured by nanoindentation, suggests that the new layers formed in group 6 samples were harder than the underlying artificially created WSL enamel.

Conclusions

The present in vitro study demonstrated that crystalline mineral layer can be formed on artificially created lesions on human enamel in the presence of $Ca^{2+}$ and $PO_4^{3-}$ ions under physiologically viable conditions by using shADP5, a 15-AA long amelogenin-derived peptide. This study also showed that the presence of biomineralizing peptide, shADP5, allows the delivery and incorporation of fluoride ions into the remineralized layer even at low F concentrations, providing an opportunity for dental health products to incorporate both elements in some clinical or everyday utility settings.

Supplemental Data
Relevant Compounds Among Ca, P, F and O

A set of possible compounds that may form under the experimental conditions discussed here upon the mineralization are listed in Table 9 below, with relevant elemental concentration ratios. For example, Ca/P ratio for HAp is 5/3=1.6 and for FAp, Ca/P is 5/1=5. In some cases, e.g., ions only test group, (Group 2), since most of the remineralization products on the surface of enamel are a result of deposition, instead of remineralization, a variety of transition Calcium phosphate solids may form, all in their amorphous, and, hence non-equilibrium states. In other words, these are kinetically trapped phases rather than being thermodynamically stable compounds.

Supplemental TEM Data

Figure 13:
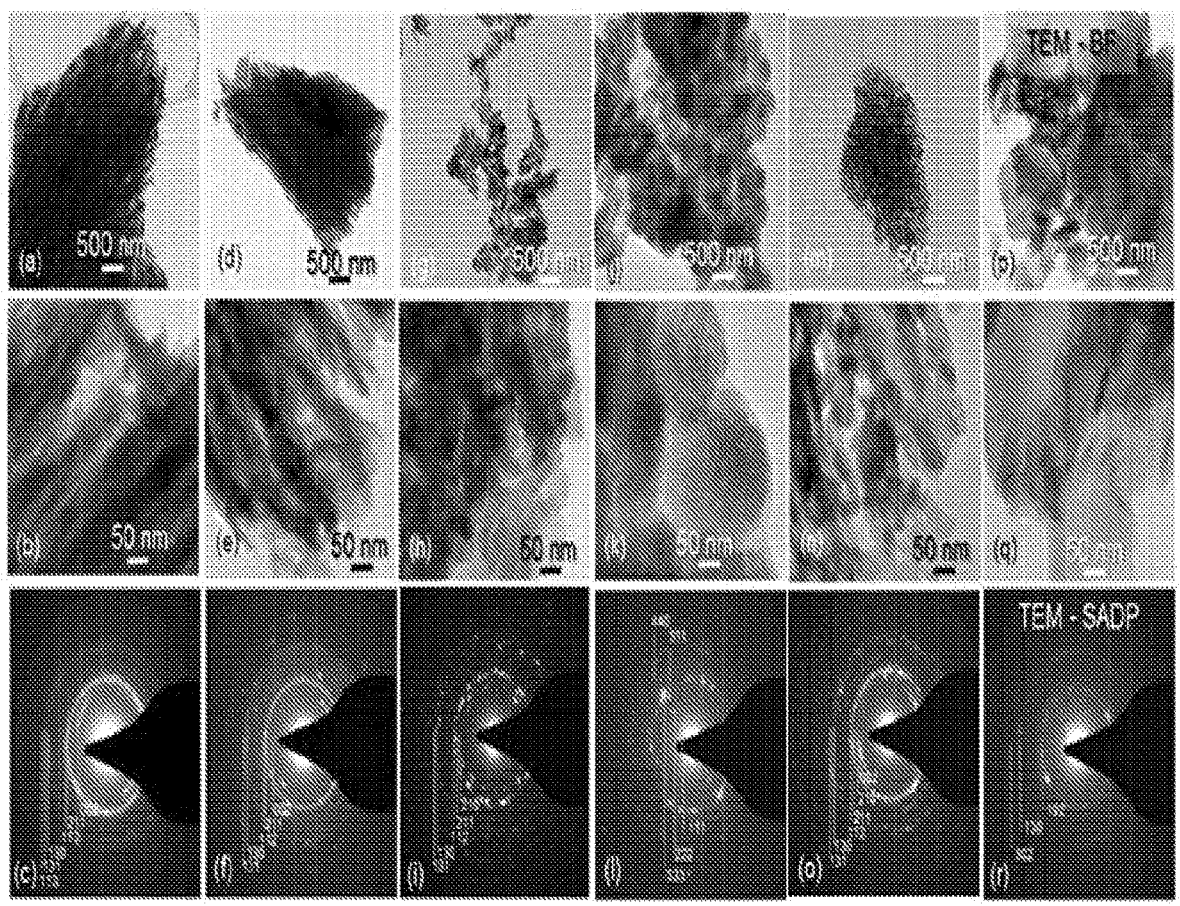
FIG. 13. TEM bright field images (top—low magnification, and middle, high magnification) and corresponding selected diffraction patterns (bottom row) showing the indices of the diffractions peaks. All top row images were recorded at the same magnifications, and middle ones were also at the same high magnification, therefore micron size marks are the same for top row and also for the middle row. The panels correspond to: (a-c) No— treatment negative control, Group 1) (d-f) Group 2 Ca and $PO_4$ ions only; (g-i) Group 3, low Fluoride concentration (1,100 ppm); (j-l) Group 4, High F concentration (20,000 ppm)), (m-o) Group 5, shADP5+low F concentration (1,100 ppm), and (p-r) Group 6, shADP5 only.

Structural and phase characterization of the samples from all groups were undertaken by transmission electron microscopy imaging and diffraction analysis. This is because x-ray diffraction characterization requires large enough volume with 10s of lam mass thickness and larger spatial sampling, 100s of μms or larger areas. Since the mineralized layer is thin, a few μms in all other group samples to 10 μm or so in group 6 samples using the peptide, TEM has been used to provide the most critical data, diffraction and phase identification. The TEM samples were prepared by gently shaving fragments off the surface of tooth specimens onto carbon-coated TEM grid to prepare and ensure electron transparent sections. All of the TEM data is included in FIG. 13 below for completeness (while only $1^{st}$, $4^{th}$ and $6^{th}$ columns of data were presented in FIG. 11).

While the no treatment sample (a-c) shows plate-like crystals of HAp that probably constitute the enamel rod, typical of the sound enamel tissue, the sample prepared with only the Ca and PO4 ions show only either small particles or structures that possibly correspond to the underlying enamel in the artificially lesioned surface. Low F and high F sample display clusters of nanoscale particles and larger particles with 100 nm diameter or larger, respectively. These results are consistent with the observation that while the smaller particles are NaF the larger particles in high F sample are $CaF_2$, as shown in the diffraction pattern. Finally in F+peptide containing sample, the surface mineralization display larger, elongated particles of HAp crystallography but with random crystallographic organization (i.e., more complete diffraction rings) while the group 6 samples displayed HAp crystallites with aligned organization, reminiscent of the HAp plate-like particles within the enamel rods, again corroborating with the SEM and EDXS results. Taken together, the most successful layer formation was accomplished using the peptide involving procedure with the resultant mineral layer being crystalline and HAp in Group 6 and possibly a FAp+HAp mixture in the shADP5+F case of samples, i.e., group 5.

Microhardness Testing and Nanoindentation Experiments

Figure 14:
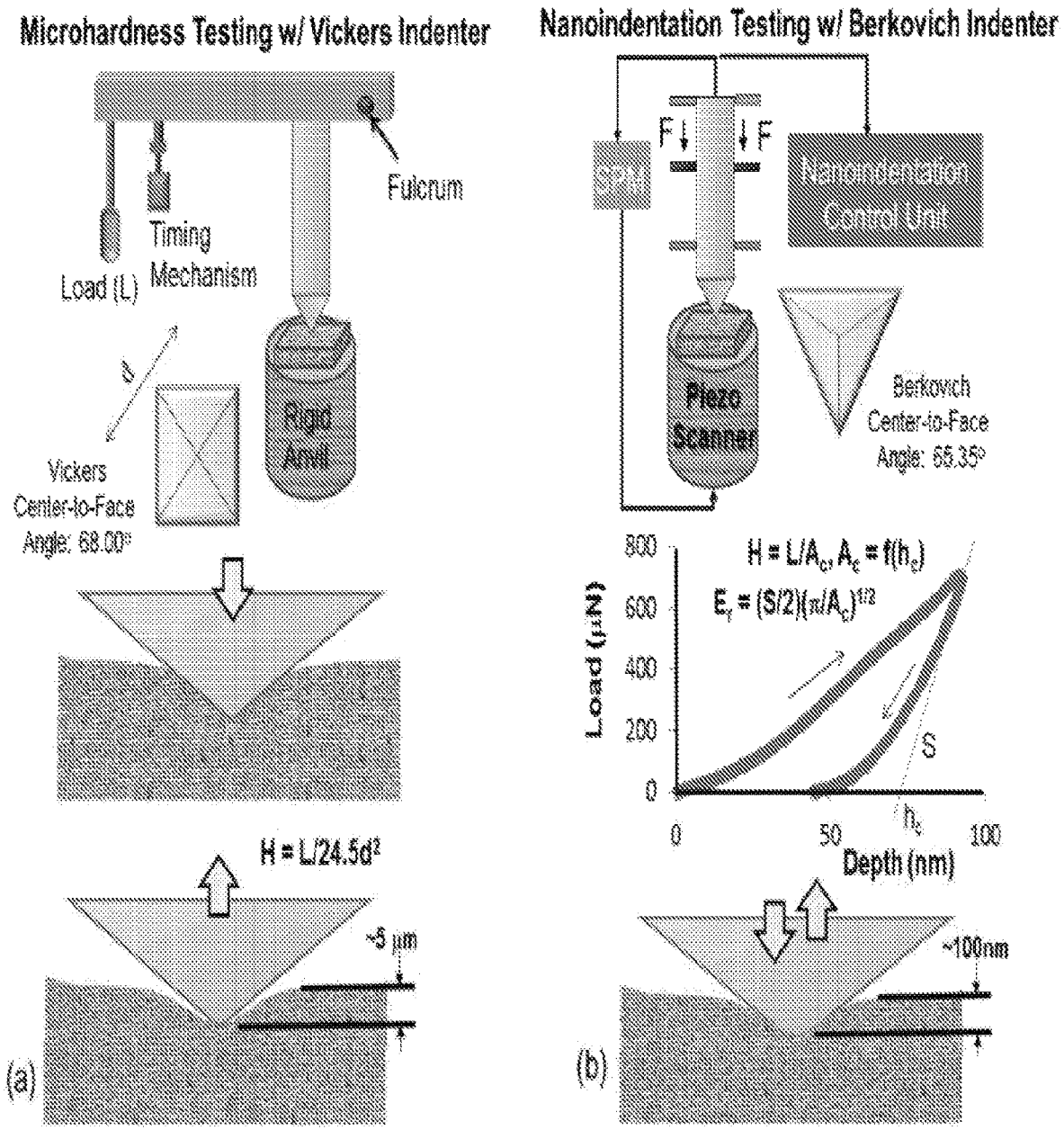
FIG. 14. Schematics of (a) microhardness and (b) nanoindentation tests.

Microhardness and nanoindentation differ in both loading range and measurement method as shown in the schematic in FIG. 14 and, for these reasons, both were used in the present work to assess the mechanical durability of the remineralized layers on artificially formed lesions on intact human teeth. In the case of microhardness (Vickers indenter), the measurement was a static one in that the load was applied, released and hardness was obtained by measuring the post-indentation projected area of the indented region (foot print). This method therefore provides information about only the plastically deformed response (plastic deformation) of the material. Furthermore the load applied

TABLE 9

| Relevant Compounds of Ca, P, F, O and Na. | | | | | | |
|---|---|---|---|---|---|---|
| Compound | Formula | Ca:P | Ca:F | Ca:O | Na:F | Na:P |
| Hydroxyapatite, HAP | $Ca_5(PO_4)_3(OH)$ | 1.60 | — | 0.38 | — | — |
| Octacalcium Phosphate, OCP | $Ca_8H_2(PO_4)_6 \cdot 5H_2O$ | 1.33 | — | 0.28 | — | — |
| Fluorapatite, FAP | $Ca_5(PO_4)_3F$ | 1.67 | 5.00 | 0.42 | — | — |
| Monocalcium Phosphate, MCP | $Ca(H_2PO_4)_2$ | 0.50 | — | 0.13 | — | — |
| Dicalcium Phosphate, DCP | $CaHPO_4$ | 1.00 | — | 0.25 | — | — |
| Tricalcium Phosphate, TCP | $Ca_3(PO_4)_2$ | 1.50 | — | 0.38 | — | — |
| Calcium Fluoride, CF | $CaF_2$ | 0.00 | 0.50 | — | — | — |
| Sodium Fluoride, NaF | NaF | — | — | — | 1.00 | 0.00 |
| Na-monofluorophosphate, MFP | $Na_2PO_4F$ | — | — | — | 2.0 | 2.00 | in this study was 10 kg, lowest allowable by the instrument. With this load, the nominal plastically deformed depth was approximately 5 µm, comparable to the thickness of the group 6 samples (shADP5 treatment) but much deeper than the mineralized layer of rest of the treatment groups. In addition, the actual interaction depth (long-range strain) during indentation was significantly deeper than 5 µm. Hence net positive contribution from the underlying artificially formed lesion on enamel (white spot lesion, WSL) in the microhardness measurement was expected.

For groups 2-5, which mineral layers were significantly thinner than 5 µm, the underlying WSL enamel was expected to have the predominant effect on the hardness, and therefore, no statistical difference was detected between the group 1 (no treatment control) and groups 2-5, while slight increase in hardness was detected in group 6 compared to group 1.

Nanoindentation, on the other hand, can handle a much smaller applied load, e.g., in the range of 700 to 800 µN; this range of loads to maintain a nominal total indentation depth of approximately 100 nm (<1 µm in indentation width) reasonable depth for both the WSL and mineralized layer regions. The method provides a dynamic measurement with the indentation system tracking continuously load vs. depth during the indentation process providing a Force-to-depth (F-d) profile of the mechanical response of the sample, including biological hard tissues such as enamel, dentin, and bone. The hardness and elastic modulus were extracted from the linear extrapolation of the unloading curve (see FIG. 14$b$). Hardness obtained by this method contains partial elastic deformation as well as plastic deformation. With small indentation depth and footprint, indentation characterization of the mineral layer only was possible in cross-section for the group 6 samples where mineral layers were more than 5 µm thick. All other treatment groups, reliable nanoindentation characterization of the layers could be partially accomplished because of the thin, and in some cases, discontinuous natural of the layers. It should also be noted that the nanomechanical properties of the artificially created lesion were also determined, with values similar to those of the mineralized layers. Regardless, the complete nanoindentation values are tabulated in Table 10 where each value represents more than 20 measurements per sample.

TABLE 10

Tabulated nanoindentation values, n ≥ 20 for each group.

| Test Groups | Hardness (GPa) | Elastic Modulus (GPa) |
| --- | --- | --- |
| Group 1 (Neg Control) | 2.10 ± 0.26 | 55.1 ± 4.3 |
| Group 2 (Ca/PO4 Only) | 2.12 ± 0.37 | 54.6 ± 6.3 |
| Group 3 (Low Conc. F) | 2.16 ± 0.28 | 53.6 ± 6.7 |
| Group 4 (High Conc. F) | 2.08 ± 0.29 | 54.0 ± 6.5 |
| Group 5 (shADP5 + Low Conc. F) | 2.15 ± 0.30 | 55.1 ± 5.9 |
| Group 6 (shADP5) (layer) | 2.23 ± 0.23 | 58.6 ± 4.7 |
| (underlying enamel) | 2.12 ± 0.21 | 55.0 ± 4.6 |
| Sound Enamel | 3.8 ± 0.72 | 91.6 ± 10.5 |
| Sound Dentin | 1.6 ± 0.33 | 21.8 ± 3.7 |

Example 10. Layer-by-Layer Mineralization by Peptide in Solution Formulation

Summary:

Using sADP peptide (SEQ ID NO:24) in aqueous solution, repeated remineralization in separate cycles produced layered mineralization that is fully integrated into the existing enamel structure on human tooth in vitro. The implication of the results is that repeated use of dental products in a variety of formulations could produce layered architecture of the remineralized structure on the surface of the teeth. The procedure and the products can thus be incorporated in dental health care products including mouth wash, whitening solutions using peptides, tooth pastes, gels and other relevant delivery systems such as dental trays and retainers.

Materials & Methods:

On extracted human tooth, the entire tooth was painted with lacquer (nail polish) except a 3 mm by 3 mm window on enamel. This window was subjected to etching then remineralization. The following steps were then carried out:

1. Etch enamel surface aqueous solution of 2.2 mM $K_2HPO_4$, 2.2 mM $CaCl_2$, and 50 mM acetic acid at pH 4.5 for 2 weeks, changing solution every other day, to create white spot lesion (WSL) of pH 7.4 Tris buffer via a laboratory squeeze bottle for 30 seconds.
2. Soak in 100 ml of 0.8 mM sADP5 solution at 37 C for 10 minutes then blot dry with tissue paper.
3. Soak in 600 ml of 4.8 mM $CaCl_2$+2.8 mM $K_2HPO_4$ in pH 7.4 Tris buffer at 37 C for 1 hour.
4. Drip rinse with DI water for 20 seconds then blot dry with Kimwipe™ sheet.
5. Repeat steps 3-4 to add more mineralized layers.

Results & Discussions—

Imaging Analysis: 4 distinctive mineral layers of approximately 2 mm thick new mineral layers were formed after 4 repetitions of Steps 3-5 in the mineralization procedure.

1. Ca/P of new mineral layers is 1.43+0.15, closer to that of OCP (Stoichiometric Ca/P of OCP=1.33, HAP=1.67)
2. Ca/P of underlying enamel is close to that of HAP Conclusions:

The sound enamel and the newly formed layered mineral have the same microstructure with well integrated interface, resulting in mechanically stable bonding. The mineralized multilayer and the sound enamel have similar chemical compositions, indicating chemical integration, and therefore stability.

Implications/Potential Applications:

1. Remineralize enamel surface via dental tray (also called mouth guard or retainers): user places peptide solution or other types of formulations (paste, gel, cream, varnish) in the dental tray that would conform and fit onto the teeth, for example, before bed or even during the daytime between meals (after brushing). Repeat x number of nights/days to build up new mineral layers to achieve desired thickness. Potential treatment for hypersensitive teeth, incipient caries, white spot lesion, and, in general preventive, daily dental health care
2. Mouth rinse, mouth wash, teeth whitening: User rinse mouth with the peptide and mineralization solution for x time after brushing to build up mineral layer. This procedure can be a preventative treatment or remineralization repair treatment for hypersensitive teeth, incipient caries, white spot lesion, as well as for whitening teeth.

Example 11. Side-by-Side Comparison of Peptide (sADP5)-Mineralized Whitening Versus Commercial Whitening Products The effect of whitening has been compared using the methods of the invention with sADP5 (SEQ ID NO:24) to the hydrogen peroxide (HP)-based treatments that are frequently used in the market. These are over-the-counter and in-clinic products, i.e., a whitening strip and a gel, with midlevel and high hydrogen peroxide contents, 14% and 30%, respectively. The specific commercial products used are CREST® 3D Whitening strip and ULTRADENT® OPALESCENCE®. The reasons for the choice of these two products is as follows: The first product, whitening strip, was chosen to represent a mid-level HP content that is commercially available as OTC product for everyday use. The gel, the second product, contains very high amount of HP, which represents the clinical, chair-side whitening application. The team considered these two products that are available in the market as good choices for comparing with SBSI's devices, containing mineralizing peptides, sADP5, which include chair-side treatment(s) using dental tray and take-home product in the gel-form.

Procedure:

The whitening products were used according to the manufacturers' directions. For the strip, the product was applied to the pre-stained tooth for 30 mins and peeled off. Then the samples were rinsed with water for 1 min to clean the surface of the teeth from any residues from the strip. In the case of the second product, the gel was applied to the pre-stained teeth for 10 minutes and then cleaned by rinsing with water for 1 minute. In the peptide-remineralization case, the stained teeth were incubated with sADP5 (SEQ ID NO:24) peptide solution (0.8 mM) for 10 mins., followed by soaking in the artificial saliva (for 1 hr) that was supplemented with 4.8 mM Ca and 2.9 mM $PO_4$ ionic concentrations.

Figure 15:
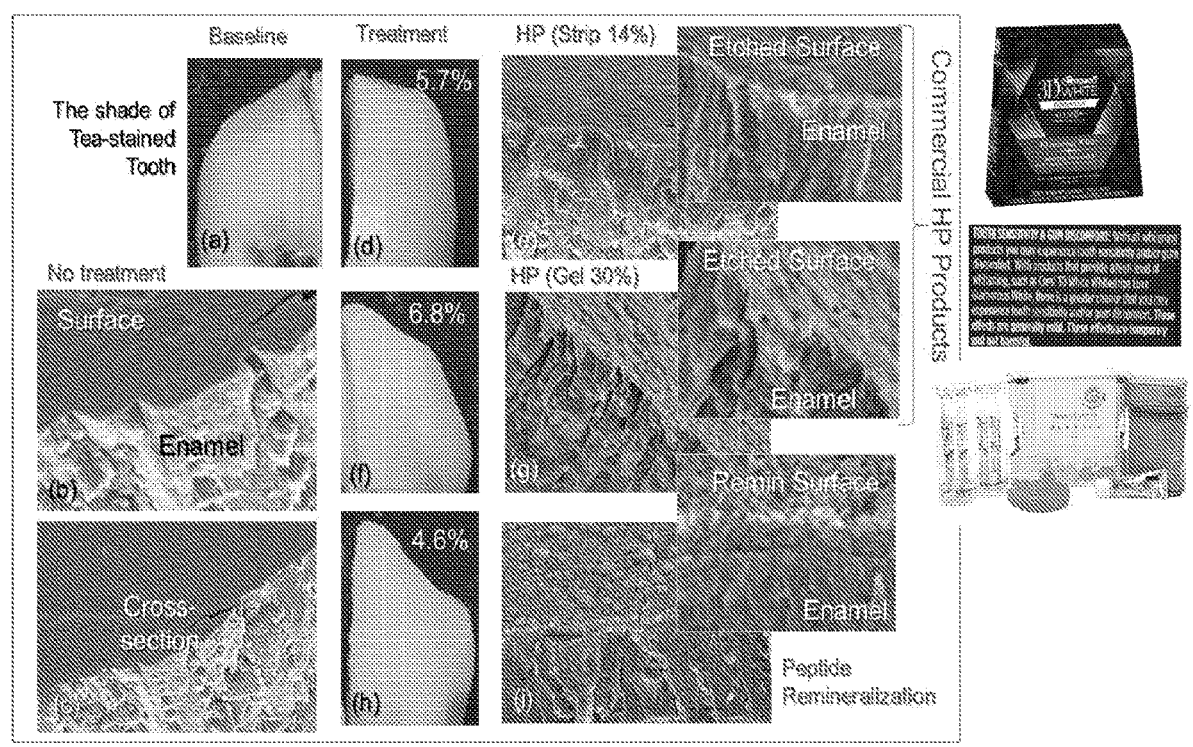
FIG. 15. Stained teeth before & after whitening treatments using commercial versus biomineralization methods. (a-c) The untreated, tea-stained group (baseline). HP-based whitening products, by CREST® 3D Whitening™ strips (d&e) containing 14% HP, and by OPALESCENCE® Whitening gel containing 30% HP (f&g). The color shade was increased compared to baseline by 5.7% and 6.8%, respectively. Compared to the tea stained teeth, not only was whitening is increased with peptide-treatment (h&i) by 4.6%, but also with the benefit of remineralization. The SEM images in the insets display the details of the tooth surface showing the effects of etching effect of the commercial products resulting in the rough surface in (e) & (g) while new mineralized layer formed by the peptide treatment in (i).

Analysis & Results:

The samples treated with whitening products or with the remineralization method were prepared for optical imaging for color change and also for surface characterization with scanning electron microscopy. The images of the teeth samples were recorded using a light optical microscopy technique under compact fluorescent light. The recorded images were digitized and examined with Image-J Line (NIH Software) for quantitative analysis of the color change (a, d, f and h). The cross-sectioned samples were prepared for SEM examination of the internal as well as surface structure of the teeth, and the results are shown in FIG. 15 (e, g, and i, plus their inset images).

The image in (a) shows that the tooth sample after tea staining has a darker shade, which was then used as the baseline value of the tooth shade in subsequent experiments. The whitening strip increased the shade by 5.65% while the gel treatment by 6.77%. Similar trend in whitening improvement of the shade was also observed in the mineralization, which produced 4.64% increase above the baseline value. A careful examination of the surfaces of the teeth test samples (insets of (e) and (g)) examined by SEM reveal etching of native enamel which appear as rough surfaces because of the demineralizing effect of the HP based strip or gel products. The peptide-treated test sample, on the other hand, produces a newly formed remineralized surface (inset in image (i)). Therefore, peptide-based treatment has two simultaneous effects: whitening as well as remineralization, strengthening the enamel and, hence, resulting in healthier teeth.

The manufacturer of the commercial products cautions users of the increased risk for tooth sensitivity and gum discomfort, both of which are clinically attributed to enamel degradation by hydrogen peroxide (see the caution label on the right of the figure above). According to CREST® and ULTRADENT® there are no ingredients in their products that safeguard against enamel degradation due the action of the active ingredient, hydrogen peroxide, which while whitening the teeth, also adversely removes the existing mineral from the surface of the teeth with potential In conclusion, the remineralization approach undertaken by the methods of the invention appears to be superior to commercial products. While the use HP-based products result in whitening, this is achieved at the expense of a subtractive process in which demineralizing of the tooth surface causes loss of dental tissue with potential long-term adverse dental health consequences. The peptide-based approach of the present invention, even in the case of solution methodology produces comparable whitening to commercial products while also restoring the mineral structure towards better dental health.

Example 12. Treating Dental Hypersensitivity

Summary:

The materials and methods for treating dental hypersensitivity involve forming a mineral layer on the teeth with the enamel (crown of the teeth) removed exposing the dental tubules. The newly formed mineralized layer occludes exposed dentinal tubules in this peptide-based approach forming a mechanically and thermally stable mineral structure covering the tooth damaged surface. The approach involves, first, creating artificial lesions by removing enamel by chemical etching to expose underlying dentin of the extracted human tooth to mimic hypersensitivity conditions. The samples were next treated with peptide-guided mineralization resulting in tens of micrometer-thick new layer over the damaged dentin. The stability of the newly formed layer were then mechanically and thermally evaluated using nanomechanical testing and thermal-cycling, respectively. The results demonstrate that exposed dentinal tubules are successfully occluded by mechanically and thermally stable mineral layer. The methods of the invention described herein offers a unique solution to dentinal hypersensitivity.

Background:

Dental hypersensitivity (DS) is one of the most common diseases in the United States, affecting the majority adult population. The disease occurs when enamel layer, crown of the teeth, wears off exposing the underlying dentin tubules. Nerves lie at the base of these dentinal tubules and when externally triggered, e.g., cold, hot, acid, basic conditions in the saliva, produce a sharp pain at the root of the tooth. Current approaches include desensitizing nerve ends by blocking the axonic action via potassium salts, limiting the permeability of dentinal tubules using synthetic adhesive sealers, e.g. NaF, bioactive glasses, oxalic acid and glass ionomer cements, or forming coagulates inside the tubules using protein cross-linker agents. Clinical validation for these agents is still lacking and their short durability against daily tooth brushing, various foods, or drinking of acidic beverages makes their occlusion effects incomplete.

Figure 16:
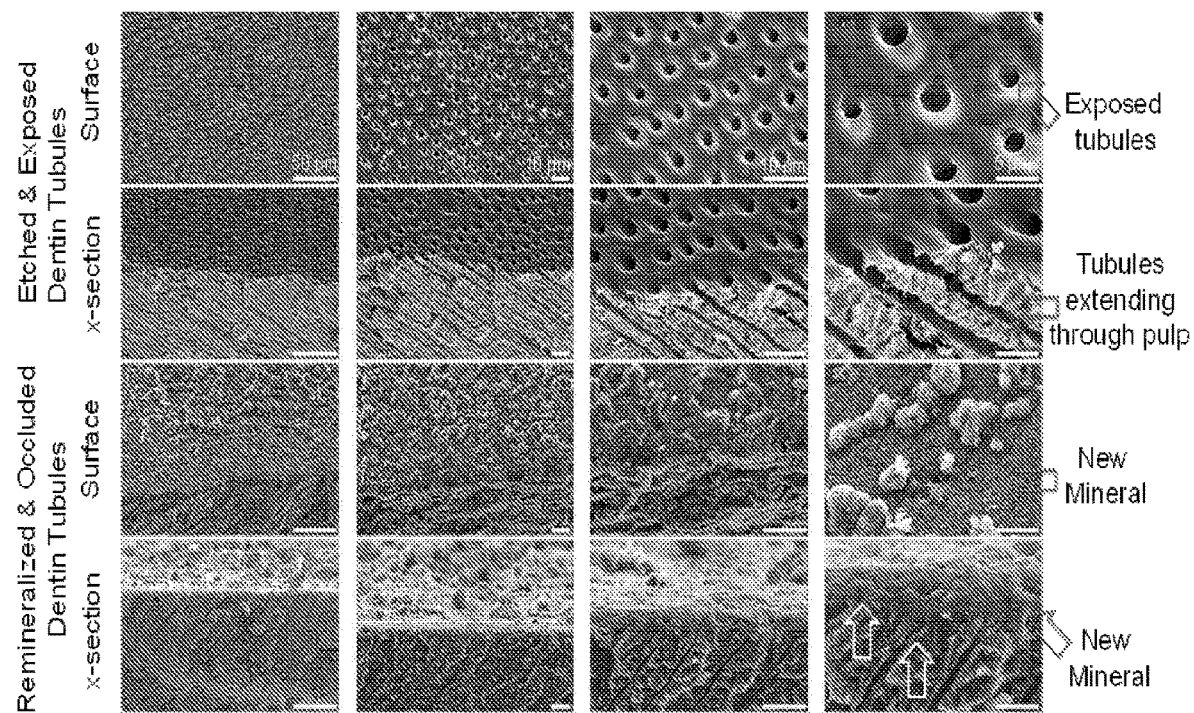
FIG. 16. Representative SEM images of hypersensitive teeth surface before (first and second rows) and after (third and fourth rows) peptide guided remineralization treatment.

Methods:

Extracted human teeth samples were collected from University of Washington clinics. The enamel tissue was cut out the using low speed saw on a perpendicular direction to the underlying dentin tubules. Next, the smear layer on the dentin was removed by polishing down to 0.1 um finish and etching for 10 seconds using 10% citric acid solution. For remineralization treatment, samples were soaked into 200 ul of 0.8 mM sADP5 peptide (SEQ ID NO:24) solution and incubated for 10 minutes at 37° C. Next, excess peptide was removed by blotting and the sample was soaked in 24 mM Tris Buffer solution supplemented with 4.8 mM Ca and 2.88 mM $PO_4$ ions for 1 hour at 37° C. Following the remineralization treatment, samples were rinsed with deionized water, dried in air and characterized with scanning electron microscope Results & Discussions:

The teeth samples for mineralization were produced by removing the enamel tissue and performing a series of polishing and etching. As a result, as shown in FIG. 16 (first and second rows) dentin tubules are clearly exposed. Following the 1 hour in vitro peptide remineralization treatment, these exposed dentin tubules are successfully occluded with a newly-formed mineral which is in the form of a continuous ~5 um layer penetrates down to tubules for ~2-3 um deep (FIG. 16 (third and fourth rows).

Conclusion & Significance:

We developed a peptide-based aqueous mineralization methodology to treat dental hypersensitivity by forming a continuous mineral layer on the exposed dentin of human teeth in vitro. This biomimetic treatment provides a unique solution to dentinal hypersensitivity which can be used as a platform technology for in-clinic and over-the-counter hypersensitivity treatments.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

Unless otherwise indicated, to the extent that definitions of terms used herein differ between this application and references that have been incorporated herein in their entirety, the definitions of terms used herein presented in this application take precedence over the definitions presented in the references incorporated herein.

Other embodiments are set forth in the following claims.

We claim:

1. A polypeptide consisting of the amino acid sequence of (SYENSHSQAINVDRT)1-10; (shADP5; SEQ ID NO: 16)

or (SYEKSHSQAINTDRT)1-10. (sADP5; SEQ ID NO: 24)

2. A fusion protein comprising one or more polypeptide of claim 1 fused to a heterologous polypeptide.

3. An oral care product, comprising
   (a) the polypeptide of claim 1,
   (b) at least one calcium ion source, and
   (c) at least one phosphate ion source.

4. The oral care product of claim 3, wherein the calcium ion source is selected from the group consisting of calcium acetate, calcium carbonate, calcium citrate, calcium chloride, calcium gluconate, calcium glycerophosphate, calcium lactate, and calcium phosphate.

5. The oral care product of claim 3, wherein the phosphate ion source is selected from the group consisting of aluminum phosphates, calcium phosphates, potassium phosphates, and sodium phosphates.

6. The oral care product of claim 3, wherein the oral care product has
   (i) a $Ca^{2+}$ concentration ranging between about 1 mM and about 2 M; and
   (ii) a $PO_4^{3-}$ concentration ranging between about 0.5 mM and about 2 M.

7. The oral care product of claim 3, wherein the oral care product is selected from the group consisting of toothpaste, toothpowders, mouthwash, gel, dental floss, liquid dentifrices, dental tablets, topical gels, troches, chewing gums, dental pastes, gingival massage creams, gargle tablets, lozenges, tooth trays, tooth varnishes, and food products.

8. The polypeptide of claim 1, consisting of the amino acid sequence $(SYENSYSQAINVDRT)_{1-10}$ (shADP5; SEQ ID NO:16).

9. The polypeptide of claim 1, consisting of the amino acid sequence SYENSHSQAINVDRT (shADP5; SEQ ID NO:16).

10. The polypeptide of claim 1, consisting of the amino acid sequence $(SYEKSHSQAINTDRT)_{1-10}$ (shADP5; SEQ ID NO:24).

11. The polypeptide of claim 1, consisting of the amino acid sequence SYEKSHSQAINTDRT (shADP5; SEQ ID NO:24).

12. A fusion protein comprising the polypeptide of claim 11 fused to a heterologous polypeptide.

13. An oral care product, comprising
   (a) the polypeptide of claim 11,
   (b) at least one calcium ion source, and
   (c) at least one phosphate ion source.

14. The oral care product of claim 13, wherein the oral care product has
   (i) a $Ca^{2+}$ concentration ranging between about 1 mM and about 2 M; and
   (ii) a $PO_4^{3-}$ concentration ranging between about 0.5 mM and about 2 M.

15. The oral care product of claim 14, wherein the oral care product is selected from the group consisting of toothpaste, toothpowders, mouthwash, gel, dental floss, liquid dentifrices, dental tablets, topical gels, troches, chewing gums, dental pastes, gingival massage creams, gargle tablets, lozenges, tooth trays, tooth varnishes, and food products.

16. A polypeptide comprising
   (a) 2-10 contiguous copies of the amino acid sequence SYENSHSQAINVDRT (shADP5; SEQ ID NO:16); or
   (b) 2-10 contiguous copies of the amino acid sequence SYEKSHSQAINTDRT (shADP5; SEQ ID NO:24).

17. An oral care product, comprising
   (a) the polypeptide of claim 16,
   (b) at least one calcium ion source, and
   (c) at least one phosphate ion source.

18. The oral care product of claim 17, wherein the oral care product has
   (i) a $Ca^{2+}$ concentration ranging between about 1 mM and about 2 M; and
   (ii) a $PO_4^{3-}$ concentration ranging between about 0.5 mM and about 2 M.

19. The oral care product of claim 18, wherein the oral care product is selected from the group consisting of toothpaste, toothpowders, mouthwash, gel, dental floss, liquid dentifrices, dental tablets, topical gels, troches, chewing gums, dental pastes, gingival massage creams, gargle tablets, lozenges, tooth trays, tooth varnishes, and food products.

\* \* \* \* \*